(12) United States Patent
Verma et al.

(10) Patent No.: US 11,420,159 B2
(45) Date of Patent: Aug. 23, 2022

(54) INTENSIFICATION OF BIOCATALYTIC GAS ABSORPTION

(71) Applicant: SAIPEM S.P.A., Milan (IT)

(72) Inventors: Mausam Verma, Québec (CA); Louis Fradette, Québec (CA); Sylvie Fradette, Québec (CA); Sylvain Lefebvre, Québec (CA); Vincent Sylvestre-Laurence, Québec (CA)

(73) Assignee: SAIPEM S.P.A., Milan (IT)

( * ) Notice: Subject to any disclaimer, the term of this patent is extended or adjusted under 35 U.S.C. 154(b) by 0 days.

(21) Appl. No.: 15/562,804

(22) PCT Filed: Mar. 30, 2016

(86) PCT No.: PCT/CA2016/050370
§ 371 (c)(1),
(2) Date: Sep. 28, 2017

(87) PCT Pub. No.: WO2016/154753
PCT Pub. Date: Oct. 6, 2016

(65) Prior Publication Data
US 2018/0280871 A1    Oct. 4, 2018

(30) Foreign Application Priority Data
Mar. 30, 2015    (CA) ................ CA 2886708

(51) Int. Cl.
| | | |
|---|---|---|
| C12P 3/00 | (2006.01) | |
| B01D 53/84 | (2006.01) | |
| B01D 53/62 | (2006.01) | |
| B01D 53/77 | (2006.01) | |
| B01D 53/14 | (2006.01) | |
| B01D 19/04 | (2006.01) | |
| B01D 53/78 | (2006.01) | |
| B01D 53/96 | (2006.01) | |

(52) U.S. Cl.
CPC ............ *B01D 53/84* (2013.01); *B01D 19/04* (2013.01); *B01D 53/1475* (2013.01); *B01D 53/62* (2013.01); *B01D 53/77* (2013.01); *B01D 53/78* (2013.01); *B01D 53/96* (2013.01); *C12P 3/00* (2013.01); *B01D 2251/304* (2013.01); *B01D 2251/306* (2013.01); *B01D 2251/606* (2013.01); *B01D 2252/20421* (2013.01); *B01D 2252/20426* (2013.01); *B01D 2252/20431* (2013.01); *B01D 2252/20478* (2013.01); *B01D 2252/20484* (2013.01); *B01D 2252/20494* (2013.01); *B01D 2252/602* (2013.01); *B01D 2252/608* (2013.01); *B01D 2255/804* (2013.01); *B01D 2257/504* (2013.01); *Y02A 50/20* (2018.01); *Y02C 20/40* (2020.08)

(58) Field of Classification Search
CPC ........ B01D 53/1493; B01D 53/62; A61L 9/01
See application file for complete search history.

(56) References Cited

U.S. PATENT DOCUMENTS

| | | | |
|---|---|---|---|
| 8,846,377 B2* | 9/2014 | Fradette | C01B 32/50 423/200 |
| 9,480,949 B2* | 11/2016 | Fradette | C01B 32/50 |
| 2009/0155889 A1 | 6/2009 | Handagama et al. | |
| 2011/0174156 A1 | 7/2011 | Saunders et al. | |
| 2011/0303088 A1* | 12/2011 | Dutra E Mello | B01D 3/08 95/151 |
| 2012/0122195 A1* | 5/2012 | Fradette | B01D 53/1425 435/266 |
| 2014/0349366 A1* | 11/2014 | Fradette | C01B 32/50 435/168 |

FOREIGN PATENT DOCUMENTS

| | | |
|---|---|---|
| CA | 2 783 190 A1 | 7/2004 |
| CA | 2 738 061 A1 | 2/2011 |
| CA | 2 769 772 A1 | 2/2011 |
| CA | 2 773 724 A1 | 4/2012 |
| CA | 2 866 932 A1 | 9/2013 |
| CN | 101219330 A | 7/2008 |
| CN | 101219330 | 5/2011 |
| CN | 103113947 A | 5/2013 |
| EP | 2332632 | 6/2011 |
| WO | WO 2004/056455 A1 | 7/2004 |
| WO | WO-2011014956 A1 * | 2/2011 ......... B01D 53/1425 |
| WO | 2014144264 | 9/2014 |

OTHER PUBLICATIONS

Wojtasik et al., "Enzyme-enhanced CO2 absorption process in rotating packed bed", Chemical Papers (2019) 73:861-869 (Year: 2019).*

Collett et al., "Dissolved carbonic anhydrase for enhancing post-combustion carbon dioxide hydration in aqueous ammonia", Energy Procedia 4 (2011) 240-244 (Year: 2011).*

Lacroix, Olivier "$CO_2$ Capture Using Immobilized Carbonic Anhydrase in Robinson-Mahoney Basket and Packed Absorption Column Reactors" *Faculté des Sciences et de Génie, Université Laval* (23 pages) (2008).

Lutze, Philip "Synergies in Process Intensification" *Technical University of Dortmund* (9 pages) (Received Mar. 2, 2015).

Reay et al. "Process Intensification: Engineering for Efficiency, Sustainability and Flexibility" *Elsevier/Butterworth-Heinemann* (444 pages) (2008) (Abstract Only).

Wang et al. "Process Intensification for Post-combustion Carbon Capture using Rotating Packed Bed through Systems Engineering Techniques" *EPSRC Pioneering Research and Skills EP / M001458/1* (2 pages) (2015).

(Continued)

*Primary Examiner* — Ruth A Davis
(74) *Attorney, Agent, or Firm* — Myers Bigel, P.A.

(57) ABSTRACT

Intensification techniques are described for enhancing biocatalytic $CO_2$ absorption operations, and may include the use of a rotating packed bed, a rotating disc reactor, a zig-zag reactor or other reactors that utilize process intensification. Carbonic anhydrase can be deployed in the high intensity reactor free in solution, immobilized with respect to particles that flow with the liquid, and/or immobilized to internals, such as packing, that are fixed within the high intensity reactor.

22 Claims, 14 Drawing Sheets

(56) References Cited

OTHER PUBLICATIONS

International Search Report and the Written Opinion of the International Searching Authority corresponding to International Patent Application No. PCT/CA2016/050370 (8 pages) (dated Jun. 9, 2016).
Extended European Search Report corresponding to European Patent Application No. 16771143.1 (8 pages) (dated Aug. 7, 2018).
Reay et al. "Process Intensification—Engineering for Efficiency, Sustainability and Flexibility" Introduction and Chapter 2 (30 pages) (published Aug. 4, 2008).
Bekard et al. "Review: The Effects of Shear Flow on Protein Structure and Function" Biopolymers, 95(11):733-745 (2011).
Robinson "Enzymes: principles and biotechnological applications" Essays in Biochemistry, 59:1-41 (2015).
Brena et al. "Immobilization of enzymes: a literature survey" Methods in Molecular Biology, 1051:15-31 (2013) (Abstract).
Camacho-Rubio et al. "A Comparative Study of the Activity of Free and Immobilized Enzymes and Its Application to Glucose Isomerase" Chemical Engineering Science, 51(17):4159-4165 (1996).

\* cited by examiner

INTENSIFICATION OF BIOCATALYTIC GAS ABSORPTION

TECHNICAL FIELD

The technical field generally relates to process intensification of biocatalytically enhanced operations, and more particularly to $CO_2$ absorption enhanced by carbonic anhydrase and intensification techniques such as the use of rotating contactors.

BACKGROUND

Conventional technology for gas absorption mainly consists of contacting a gas and a liquid inside a contactor, such as a packed column or a spray column, in such a way that the liquid phase contacting the gas phase absorbs a gaseous species of interest. The liquid phase can be selected for its ability to absorb the gaseous species of interest and to carry the absorbed gaseous species. To enable a high contact surface area between the gas and the liquid phase, a solid support known as a packing, can be present in packed column type contactors. The packing is fixed within the reaction chamber and its geometry may differ depending on the process conditions and thus provide different contact surface areas and/or flow regimes inside the liquid film flowing at the surface of the packing to promote the mass transfer of the gaseous species of interest into the liquid phase. The packing can be random or structured and can have different geometries.

Such conventional gas absorption technology is used for $CO_2$ capture operations. In this application, the gas phase containing $CO_2$, which may be a process gas, a gas effluent or another $CO_2$ containing gas, can be fed to a packed column absorption unit where it is contacted with a liquid phase. Depending on the pressure, temperature of the $CO_2$ containing gas, the nature of the liquid phase may differ. For example, for a gas phase available at high pressure, physical solvents or ionic liquids may be used, while for cases where the gas phase is available at a low pressure, which typical of post-combustion $CO_2$-containing gas effluent, chemical solvents may be beneficial. Once the gaseous species is absorbed into the liquid it can be transferred to a second unit for regeneration of the solution by desorption/stripping techniques or mineralization. For both high and low pressure applications for $CO_2$ capture, the use of the conventional contactor technology can result in the use of large size equipment, large installation footprints which can, in turn, lead to large capital investment and operating costs. This scenario is a challenge with respect to deployment of $CO_2$ capture installations.

Most enhancements related to $CO_2$ capture are focused on (i) improving the formulation of the absorption solution to maximize absorption rate, absorption solution carrying capacity (or solution cyclic capacity) and energy requirements for the regeneration of the solution and release of the absorbed $CO_2$, as well as (ii) optimizing equipment and process configurations in order to maximize heat integration in the process and thus reduce the process energy requirement. Most of the enhancements so far have not been able to dramatically reduce the equipment size, installation footprint and energy requirements.

In recent years, process intensification has been considered to enhance various processes. Some process intensification equipment, such as Higee contactors, have been proposed for $CO_2$ capture operations, and some research has been conducted at the laboratory scale using conventional liquid solutions such as aqueous solutions including MEA or NaOH.

There is a need for a technology that further enhances gas absorption, such as $CO_2$ absorption from a $CO_2$ containing gas to reduce equipment size, installation footprint and energy requirements.

SUMMARY

In some implementations, there is provided a biocatalytic process for treating a $CO_2$ containing gas, comprising: supplying $CO_2$ containing gas into a high intensity reactor comprising a reaction chamber; supplying an absorption solution into the high intensity reactor; contacting the $CO_2$ containing gas and the absorption solution within the reaction chamber, in the presence of carbonic anhydrase at elevated biocatalytic concentration, for converting dissolved $CO_2$ into bicarbonate and hydrogen ions to form a $CO_2$ depleted gas and an ion enriched solution; and withdrawing the $CO_2$ depleted gas and an ion enriched solution from the high intensity reactor.

In some implementations, the absorption solution comprises a slow absorption compound. In some implementations, the slow absorption compound comprises tertiary amines, tertiary alkanolamines, tertiary amino-acids, tertiary amino-acid salts, carbonates or a mixture thereof.

In some implementations, the absorption solution comprises an absorption compound comprising primary, secondary and/or tertiary amines; primary, secondary and/or tertiary alkanolamines; primary, secondary and/or tertiary amino acids; carbonates.

In some implementations, the absorption compound comprises piperidine, piperazine and derivatives thereof which are substituted by at least one alkanol group, monoethanolamine (MEA), 2-amino-2-methyl-i-propanol (AMP), 2-(2-aminoethylamino)ethanol (AEE), 2-amino-2-hydroxymethyl-i,3-propanediol (Tris), N-methyldiethanolamine (MDEA), dimethylmonoethanolamine (DMMEA), diethylmonoethanolamine (DEMEA), triisopropanolamine (TIPA) and triethanolamine), dialkylether or dimethylether of polyethylene glycol; glycine, proline, arginine, histidine, lysine, aspartic acid, glutamic acid, methionine, serine, threonine, glutamine, cysteine, asparagine, leucine, isoleucine, alanine, valine, tyrosine, tryptophan, phenylalanine, and derivatives such as taurine, N,cyclohexyl 1,3-propanediamine, N secondary butyl glycine, N-methyl N-secondary butyl glycine, diethylglycine, dimethylglycine, sarcosine, methyl taurine, methyl-a-aminopropionic acid, N-(β-ethoxy)taurine, N-(β-aminoethyl)taurine, N-methyl alanine, 6-aminohexanoic acid, including potassium or sodium salts of aforementioned amino acids; potassium carbonate, sodium carbonate, ammonium carbonate; or mixtures thereof.

In some implementations, at least a portion of the carbonic anhydrase is free in the absorption solution. In some implementations, at least a portion of the carbonic anhydrase is provided on or in particles flowing with absorption solution through the high intensity reactor. In some implementations, at least a portion of the carbonic anhydrase is provided immobilized with respect to supports fixed within the reaction chamber.

In some implementations, the high intensity reactor comprises internals fixed within the reaction chamber. In some implementations, the internals comprise packing material.

In some implementations, the high intensity reactor comprises a rotating packed bed reactor comprising the packing material housed in the reaction chamber. In some implementations, the packing material comprises metal foam. In some implementations, the reaction chamber comprises more than one packed bed or comprises a split packing.

In some implementations, the packing material has between 80% and 95% porosity. In some implementations, the packing material has between 85% and 90% porosity.

In some implementations, the internals comprise discs. In some implementations, the high intensity reactor comprises a rotating disc reactor having the discs housed within the reaction chamber.

In some implementations, the carbonic anhydrase is immobilized with respect to the internals.

In some implementations, the carbonic anhydrase is immobilized by covalent bonding, adsorption, ionic bonding, entrapment or encapsulation.

In some implementations, the carbonic anhydrase is immobilized with respect to an immobilization material that is provided as a coating on the internals.

In some implementations, the carbonic anhydrase is immobilized with respect to the particles by covalent bonding, adsorption, ionic bonding, entrapment or encapsulation.

In some implementations, the carbonic anhydrase is immobilized with respect to an immobilization material that is provided as a coating on the particles.

In some implementations, the elevated concentration of the carbonic anhydrase is at least 0.1 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 0.2 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 0.5 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 1 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 2 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 3 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 4 g/L, and the high intensity reactor is operated to provide mass transfer of $CO_2$ into the absorption solution at a rate such that biocatalytic impact on $CO_2$ hydration rate is below a plateau.

In some implementations, the elevated concentration of the carbonic anhydrase is at least 6 g/L, and the high intensity reactor is operated to provide mass transfer of $CO_2$ into the absorption solution at a rate such that biocatalytic impact on $CO_2$ hydration rate is below a plateau.

In some implementations, there is provided a biocatalytic system for treating a $CO_2$ containing gas, comprising: a gas inlet receiving $CO_2$ containing gas; a liquid inlet receiving an absorption solution; a high intensity reaction chamber in fluid communication with the gas inlet and the liquid inlet, the reaction chamber being configured to enable contact of the $CO_2$ containing gas and the absorption solution; carbonic anhydrase present in the reaction chamber at elevated biocatalytic concentration, and catalysing the conversion of dissolved $CO_2$ into bicarbonate and hydrogen ions to form a $CO_2$ depleted gas and an ion enriched solution; a gas outlet in fluid communication with the reaction chamber for withdrawing the $CO_2$ depleted gas; and a liquid outlet in fluid communication with the reaction chamber for withdrawing the ion enriched solution from the high intensity reactor.

In some implementations, the absorption solution comprises a slow absorption compound. In some implementations, the slow absorption compound comprises tertiary amines, tertiary alkanolamines, tertiary amino-acids, tertiary amino-acid salts, carbonates or a mixture thereof. In some implementations, the absorption solution comprises an absorption compound comprising primary, secondary and/or tertiary amines; primary, secondary and/or tertiary alkanolamines; primary, secondary and/or tertiary amino acids; carbonates. In some implementations, the absorption compound comprises piperidine, piperazine and derivatives thereof which are substituted by at least one alkanol group, monoethanolamine (MEA), 2-amino-2-methyl-i-propanol (AMP), 2-(2-aminoethylamino)ethanol (AEE), 2-amino-2-hydroxymethyl-i,3-propanediol (Tris), N-methyldiethanolamine (MDEA), dimethylmonoethanolamine (DM-MEA), diethylmonoethanolamine (DEMEA), triisopropanolamine (TIPA) and triethanolamine), dialkylether or dimethylether of polyethylene glycol; glycine, proline, arginine, histidine, lysine, aspartic acid, glutamic acid, methionine, serine, threonine, glutamine, cysteine, asparagine, leucine, isoleucine, alanine, valine, tyrosine, tryptophan, phenylalanine, and derivatives such as taurine, N,cyclohexyl 1,3-propanediamine, N secondary butyl glycine, N-methyl N-secondary butyl glycine, diethylglycine, dimethylglycine, sarcosine, methyl taurine, methyl-a-aminopropionic acid, N-(β-ethoxy)taurine, N-(β-aminoethyl)taurine, N-methyl alanine, 6-aminohexanoic acid, including potassium or sodium salts of aforementioned amino acids; potassium carbonate, sodium carbonate, ammonium carbonate; or mixtures thereof.

In some implementations, at least a portion of the carbonic anhydrase is free in the absorption solution. In some implementations, at least a portion of the carbonic anhydrase is provided on or in particles flowing with absorption solution through the high intensity reactor. In some implementations, at least a portion of the carbonic anhydrase is provided immobilized with respect to supports fixed within the reaction chamber.

In some implementations, the high intensity reactor comprises internals fixed within the reaction chamber.

In some implementations, the internals comprise packing material. In some implementations, the high intensity reactor comprises a rotating packed bed reactor comprising the packing material housed in the reaction chamber. In some implementations, the packing material comprises metal foam. In some implementations, the packing material has between 80% and 95% porosity. In some implementations, the packing material has between 85% and 90% porosity.

In some implementations, the internals comprise discs. In some implementations, the high intensity reactor comprises a rotating disc reactor having the discs housed within the reaction chamber.

In some implementations, the carbonic anhydrase is immobilized with respect to the internals. In some implementations, the carbonic anhydrase is immobilized by covalent bonding, adsorption, ionic bonding, entrapment or encapsulation. In some implementations, the carbonic anhydrase is immobilized with respect to an immobilization material that is provided as a coating on the internals. In some implementations, the carbonic anhydrase is immobilized with respect to the particles by covalent bonding, adsorption, ionic bonding, entrapment or encapsulation. In some implementations, the carbonic anhydrase is immobilized with respect to an immobilization material that is provided as a coating on the particles.

In some implementations, the elevated concentration of the carbonic anhydrase is at least 0.1 g/L, at least 0.2 g/L, at least 0.5 g/L, or at least 1 g/L. In some implementations, the elevated concentration of the carbonic anhydrase is at least 2 g/L. In some implementations, the elevated concentration of the carbonic anhydrase is at least 3 g/L. In some implementations, the elevated concentration of the carbonic anhydrase is at least 4 g/L. In some implementations, the elevated concentration of the carbonic anhydrase is at least 6 g/L.

In some implementations, there is provided a use of carbonic anhydrase at elevated biocatalytic concentration in a rotating packed bed reactor for biocatalytically enhancing $CO_2$ absorption from a gas into an absorption solution.

In some implementations, there is provided a biocatalytic process for treating a $CO_2$ containing gas, comprising: supplying $CO_2$ containing gas into a high intensity reactor comprising a reaction chamber; supplying an absorption solution into the high intensity reactor; contacting the $CO_2$ containing gas and the absorption solution within the reaction chamber, in the presence of carbonic anhydrase immobilized with respect to particles that are carried with the absorption solution through the reaction chamber, for converting dissolved $CO_2$ into bicarbonate and hydrogen ions to form a $CO_2$ depleted gas and an ion enriched solution; and withdrawing the $CO_2$ depleted gas and an ion enriched solution from the high intensity reactor.

In some implementations, there is provided a biocatalytic system for treating a $CO_2$ containing gas, comprising: a gas inlet receiving $CO_2$ containing gas; a liquid inlet receiving an absorption solution; a high intensity reaction chamber in fluid communication with the gas inlet and the liquid inlet, the reaction chamber being configured to enable contact of the $CO_2$ containing gas and the absorption solution; carbonic anhydrase immobilized with respect to particles that are carried with the absorption solution through the reaction chamber, and catalysing the conversion of dissolved $CO_2$ into bicarbonate and hydrogen ions to form a $CO_2$ depleted gas and an ion enriched solution; a gas outlet in fluid communication with the reaction chamber for withdrawing the $CO_2$ depleted gas; and a liquid outlet in fluid communication with the reaction chamber for withdrawing the ion enriched solution from the high intensity reactor.

In some implementations, there is provided a biocatalytic process for treating a $CO_2$ containing gas, comprising: supplying $CO_2$ containing gas into a high intensity reactor comprising a rotating reaction chamber; supplying an absorption solution into the high intensity reactor; contacting the $CO_2$ containing gas and the absorption solution within the rotating reaction chamber, in the presence of carbonic anhydrase, for converting dissolved $CO_2$ into bicarbonate and hydrogen ions to form a $CO_2$ depleted gas and an ion enriched solution; operating the high intensity reactor at a liquid-to-gas (L/G) ratio, a carbonic anhydrase concentration, and a rotation speed of the rotating reaction chamber, such that the rotation speed is at or below an upper rotation speed limit at which biocatalytic acceleration of the hydration reaction reaches a maximum plateau for the L/G ratio; and withdrawing the $CO_2$ depleted gas and an ion enriched solution from the high intensity reactor.

In some implementations, the absorption solution comprises a carbonate absorption compound. In some implementations, the carbonic anhydrase concentration is between about 0.1 g/L and about 6 g/L, or between about 3 g/L and about 6 g/L, based on the volume of the absorption solution prior to enzyme addition. In some implementations, the L/G ratio is between about 7 and about 300, or between about 30 and about 3000, on a w/w basis. In some implementations, the rotation speed is between about 200 RPM and about 1000 RPM. In some implementations, the rotation speed is preferably between about 300 RPM and about 750 RPM. In some implementations, the rotating reaction chamber comprises a packing material having a voidage between about 80% and about 95%.

In some implementations, there is provided a biocatalytic process for treating a $CO_2$ containing gas, comprising: supplying $CO_2$ containing gas into a high intensity reactor comprising a rotating reaction chamber; supplying an absorption solution into the high intensity reactor; contacting the $CO_2$ containing gas and the absorption solution within the rotating reaction chamber, in the presence of carbonic anhydrase, for converting dissolved $CO_2$ into bicarbonate and hydrogen ions to form a $CO_2$ depleted gas and an ion enriched solution; operating the high intensity reactor at a liquid-to-gas (L/G) ratio; operating the high intensity reactor at a rotation speed for the rotating reaction chamber, wherein the rotation speed is based on the L/G ratio to maximize biocatalytic acceleration of the hydration reaction; and withdrawing the $CO_2$ depleted gas and an ion enriched solution from the rotating reaction chamber.

In some implementations, the rotation speed is below an upper rotation speed limit at which biocatalytic acceleration of the hydration reaction reaches a maximum plateau for the L/G ratio.

In some implementations, there is provided a biocatalytic process for treating a $CO_2$ containing gas, comprising: supplying $CO_2$ containing gas into a high intensity reactor comprising a reaction chamber comprising internals; supplying an absorption solution into the high intensity reactor to flow over the internals; contacting the $CO_2$ containing gas and the absorption solution within the reaction chamber, in the presence of carbonic anhydrase immobilized with respect to the internals, for converting dissolved $CO_2$ into bicarbonate and hydrogen ions to form a $CO_2$ depleted gas and an ion enriched solution; and withdrawing the $CO_2$ depleted gas and an ion enriched solution from the high intensity reactor.

In some implementations, the reaction chamber is configured for rotation and the internals comprise packing material or discs.

In some implementations, there is provided a biocatalytic process for treating a $CO_2$ containing gas, comprising: supplying $CO_2$ containing gas into a high intensity reactor comprising a reaction chamber; supplying an absorption solution into the high intensity reactor; contacting the $CO_2$ containing gas and the absorption solution within the reaction chamber, in the presence of carbonic anhydrase, for converting dissolved $CO_2$ into bicarbonate and hydrogen ions to form a $CO_2$ depleted gas and an ion enriched solution; operating the high intensity reactor at conditions that cause foam production; providing a defoamer in the high intensity reactor to inhibit the foam production; withdrawing the $CO_2$ depleted gas and an ion enriched solution from the high intensity reactor.

In some implementations, the carbonic anhydrase is provided free in the absorption solution at a concentration sufficiently high that would cause an increase foam production in the high intensity reactor. While foam production is not generally desirable, it may be desirable to have a higher enzyme concentration that would result in some foam production but the biocatalytic advantages would outweigh the foam production, particularly when a defoamer is used to reduce or eliminate foam that would be generated. In some implementations, the concentration of the carbonic anhydrase is above 0.1 or above 0.2 g/L.

In some implementations, the defoamer comprise an oil-in-water emulsion. In some implementations, the defoamer (anti-foam compound or foam-reducer compound) comprises a water-in-oil emulsion, polyol based compounds, a polyol based dispersion, silicon based compounds, a non-ionic silicon emulsion, and/or a silica particle suspension.

In some implementations, the defoamer compound is provided in a concentration of at least 10 mg/L or at least 50 mg/L based on the volume of the absorption solution. In some implementations, the defoamer is provided in a concentration of at least 200 mg/L based on the volume of the absorption solution. In some implementations, the defoamer is provided in a concentration of between 50 and 300 mg/L or between 100 and 300 mg/L based on the volume of the absorption solution.

In some implementations, there is provided a biocatalytic system for treating a $CO_2$ containing gas, comprising: a gas inlet receiving $CO_2$ containing gas; a liquid inlet receiving an absorption solution; a high intensity reaction chamber in fluid communication with the gas inlet and the liquid inlet, the reaction chamber being configured to enable contact of the $CO_2$ containing gas and the absorption solution; carbonic anhydrase present in the reaction chamber and catalysing the conversion of dissolved $CO_2$ into bicarbonate and hydrogen ions to form a $CO_2$ depleted gas and an ion enriched solution; a defoamer present in the high intensity reactor to inhibit foam production; a gas outlet in fluid communication with the reaction chamber for withdrawing the $CO_2$ depleted gas; and a liquid outlet in fluid communication with the reaction chamber for withdrawing the ion enriched solution from the high intensity reactor.

In some implementations, there is provided a biocatalytic process for treating a gas stream comprising a target gas component, comprising: supplying the gas stream into a high intensity reactor comprising a reaction chamber; supplying an absorption solution into the high intensity reactor; contacting the gas stream and the absorption solution within the reaction chamber, in the presence of a biocatalyst, for converting dissolved target gas component into ions to form a gas stream depleted in the target gas component and an ion enriched solution; and withdrawing the depleted gas stream and an ion enriched solution from the high intensity reactor. One or more aspects of the processes or systems described herein for $CO_2$ absorption can also be applied to target gas components in general as well as various specific target gas components that may benefit from implementation of such aspects, such as particles high intensity reactor structural features, use of absorption compounds and/or defoamers, and operating parameters. In addition, other biocatalytically enhanced unit operations can also be used in connection with high intensity reactors and various adapted features described herein, for a variety of unit operations that may include reactions, phase separation, scrubbing, stripping, and so on, where use of biocatalyst and high intensity reactor cooperate to enhance the biocatalytic impact and the mass transfer in the unit operation.

In some implementations, there is provided a biocatalytic process for treating a $CO_2$ containing gas, comprising:
supplying $CO_2$ containing gas into a rotating packed bed (RPB) comprising a reaction chamber;
supplying an absorption solution into the RPB;
contacting the $CO_2$ containing gas and the absorption solution within the reaction chamber, in the presence of carbonic anhydrase that flows with the absorption solution, under fluid acceleration conditions of at least 50 m/s$^2$, for converting dissolved $CO_2$ into bicarbonate and hydrogen ions to form a $CO_2$ depleted gas and an ion enriched solution free of bicarbonate precipitates; and
withdrawing the $CO_2$ depleted gas and an ion enriched solution from the high intensity reactor.

In some implementations, the process comprises supplying the ion enriched solution to a regeneration unit to produce a regenerated liquid stream and a CO2 gas stream.

In some implementations, all of the ion enriched solution is supplied directly to the regeneration unit.

In some implementations, the ion enriched solution passes through a heat exchanger prior to being introduced into the regeneration unit.

In some implementations, the carbonic anhydrase is free in solution. In some implementation, the carbonic anhydrase is present in an enzyme concentration between about 0.1 g/L and about 2 g/L. In some implementation, the carbonic anhydrase is present in an enzyme concentration between about 0.2 g/L and about 1.5 g/L. In some implementation, the carbonic anhydrase is present in an enzyme concentration between about 0.5 g/L and about 1 g/L.

In some implementations, the carbonic anhydrase is immobilized with respect to particles that flow with the absorption solution.

In some implementations, the absorption solution comprises a carbonate compound. In some implementations, the carbonate compound comprises a monovalent metal ion. In some implementations, the carbonate compound comprises sodium carbonate. In some implementations, the carbonate compound comprises potassium carbonate.

In some implementations, the contacting of the $CO_2$ containing gas and the absorption solution is performed in one pass through the reaction chamber.

In some implementations, there is provided a biocatalytic process for treating a $CO_2$ containing gas, comprising:
supplying $CO_2$ containing gas into a high intensity reactor comprising a reaction chamber;
supplying an absorption solution into the high intensity reactor;
contacting the $CO_2$ containing gas and the absorption solution within the reaction chamber, in the presence of carbonic anhydrase that flows with the absorption solution, for converting dissolved $CO_2$ into bicarbonate and hydrogen ions to form a $CO_2$ depleted gas and an ion enriched solution free of bicarbonate precipitates; and
withdrawing the $CO_2$ depleted gas and an ion enriched solution from the high intensity reactor.

In some implementations, the process includes supplying the ion enriched solution to a regeneration unit to produce a regenerated liquid stream and a $CO_2$ gas stream.

In some implementations, all of the ion enriched solution is supplied directly to the regeneration unit.

In some implementations, the ion enriched solution passes through a heat exchanger prior to being introduced into the regeneration unit.

In some implementations, the carbonic anhydrase is free in solution.

In some implementations, the carbonic anhydrase is present in an enzyme concentration between about 0.1 g/L and about 2 g/L. In some implementations, the carbonic anhydrase is present in an enzyme concentration between about 0.2 g/L and about 1.5 g/L. In some implementations, the carbonic anhydrase is present in an enzyme concentration between about 0.5 g/L and about 1 g/L.

In some implementations, the carbonic anhydrase is immobilized with respect to particles.

In some implementations, the absorption solution comprises a carbonate compound. In some implementations, the carbonate compound comprises a monovalent metal ion. In some implementations, the carbonate compound comprises sodium carbonate. In some implementations, the carbonate compound comprises potassium carbonate.

In some implementations, the contacting of the $CO_2$ containing gas and the absorption solution is performed in one pass through the reaction chamber.

In some implementations, the high intensity reactor is a rotating packed bed.

In some implementations, the rotating packed bed is operated to provide fluid acceleration of at least 25 m/s$^2$. In some implementations, the rotating packed bed is operated to provide fluid acceleration of at least 100 m/s$^2$. the rotating packed bed is operated to provide fluid acceleration of at least 303 m/s$^2$.

In some implementations, the rotating packed bed is operated to provide fluid acceleration of at least 1000 m/s$^2$.

In some implementations, the rotating packed bed is operated to provide fluid acceleration of at least 2000 m/s$^2$.

In some implementations, the rotating packed bed has a radius of 0.1 m to 0.2 m and is operated with a rotational speed between 450 and 1200 rotations per minute.

In some implementations, the absorption solution comprises a defoamer.

In some implementations, the L/G ratio is between about 30 and about 300 on a w/w basis.

In some implementations, the reaction chamber comprises a packing material having a voidage between about 80% and about 95%.

In some implementations, the high intensity reactor comprises a rotating disc reactor, a zig-zag contactor, or a combination thereof.

In some implementations, the process includes using a heat transfer fluid with low-grade heat for providing heat to the high intensity reactor.

In some implementations, the heat transfer fluid has a temperature level below 1000, below 90° C., below 80° C., below 70° C. or below 60° C.

In some implementations, the heat transfer fluid comprises water, heat transfer oil, freon and/or a phase-changing fluids.

It should be noted that any of the features described above and/or herein can be combined with any other features, processes and/or systems described herein, unless such features would be clearly incompatible.

DETAILED DESCRIPTION

Various techniques are described for enhancing gas component capture operations, such as $CO_2$ absorption. While the techniques will be described in detail with respect to the absorption and desorption of $CO_2$ in particular, using carbonic anhydrase enzyme for biocatalytic enhancements, it should be understood that the techniques can also apply to other catalytic processes where a liquid stream and a gas stream containing a gas component are supplied to an intensification reactor, such as a rotating packed bed, such that mass transfer limitations between the gas and liquid phases are reduced to facilitate enhanced catalytic impact on the process of transferring the gas component from the gas phase to the liquid phase.

Intensification of Biocatalytically Enhanced $CO_2$ Capture

Figure 1:
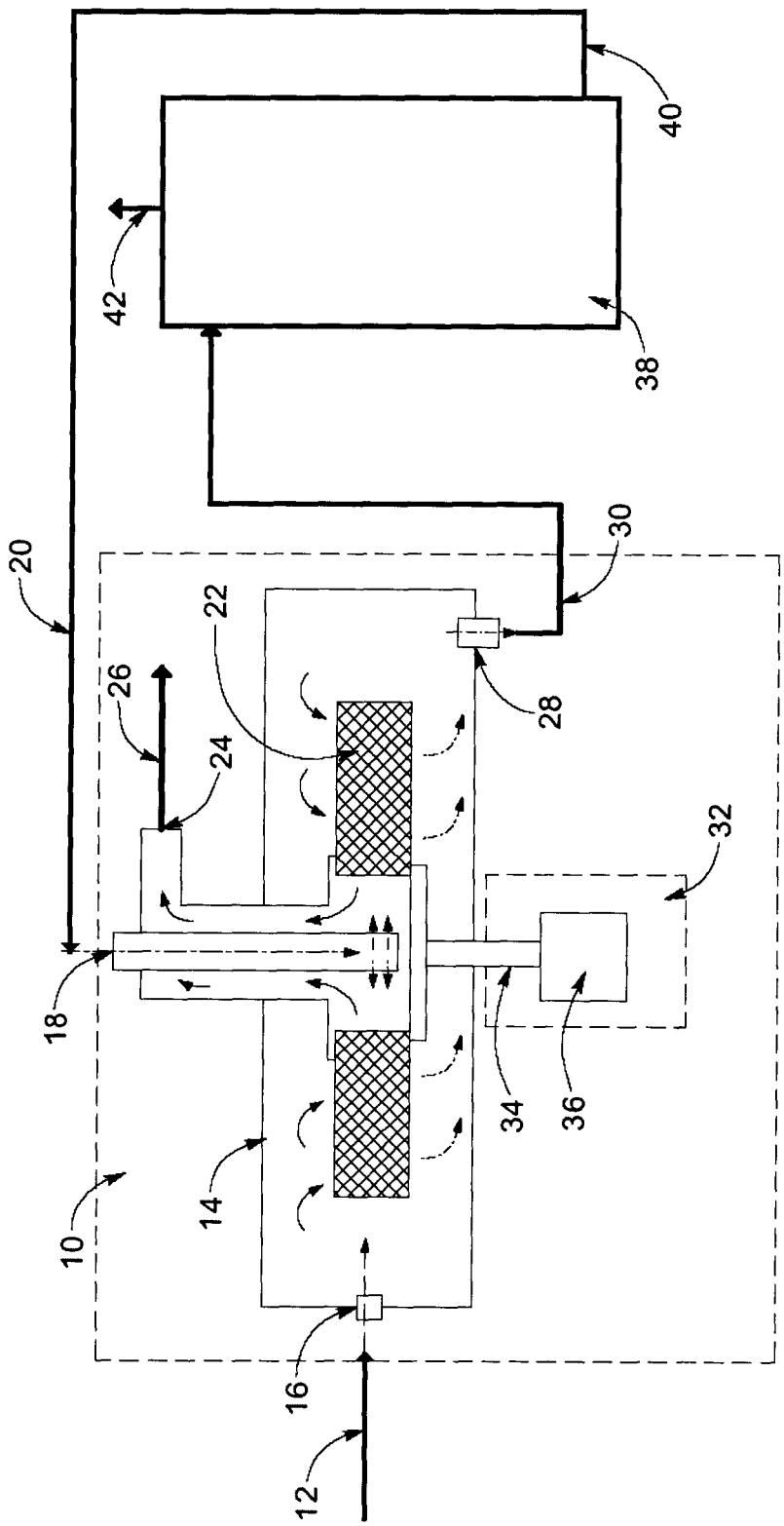
FIG. 1 is a schematic representation of an absorption and desorption system including a rotating packed bed absorber.
Figure 2:
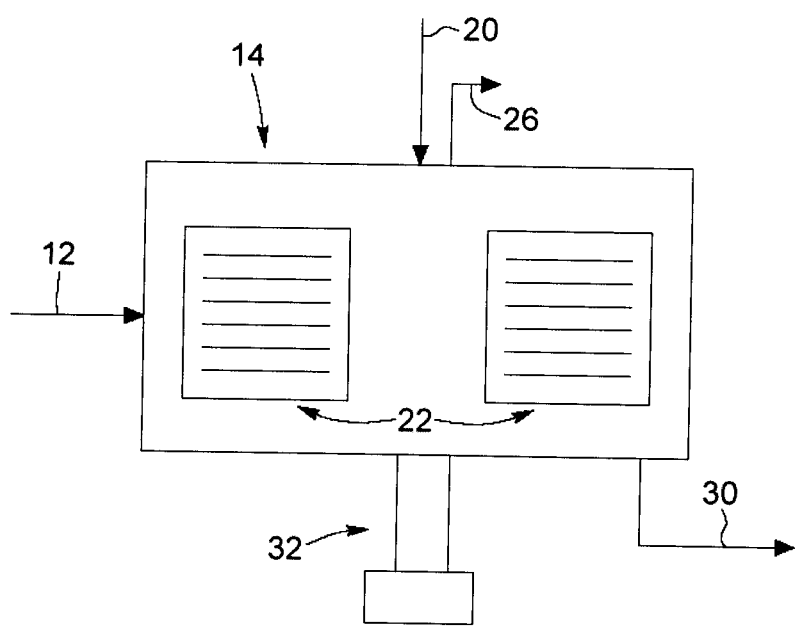
FIG. 2 is a schematic representation of a rotating discs contactor.
Figure 3:
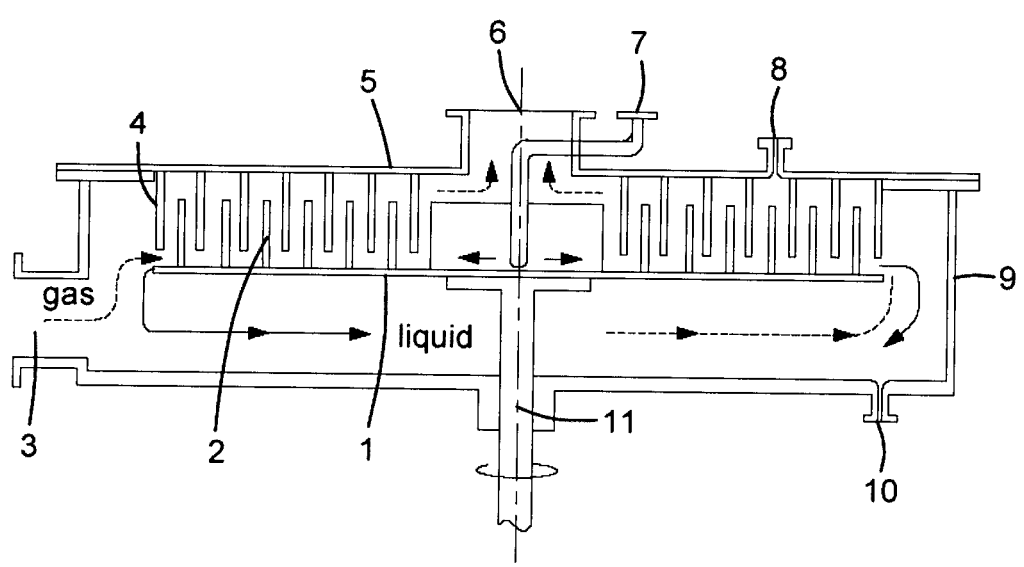
FIG. 3 is a schematic representation of a zigzag bed contactor.

Referring to FIG. 1, a biocatalytic system 10 for removing a gas component, such as $CO_2$, from a gas stream 12 by absorption is illustrated. The $CO_2$ containing gas 12 is supplied to a high intensity reactor, such as a rotating reactor 14. The rotating reactor 14 can be a rotating packed bed reactor, a rotating disc reactor, a rotating zig zag bed or another type of reactor that uses rotation to increase mass transfer rate. The rotating reactor 14 can be a rotating packed bed reactor including a gas inlet 16 for receiving the $CO_2$ containing gas 12, a liquid inlet 18 for receiving an absorption solution 20, a reaction chamber 22 including packing material, discs or a zigzag bed, a gas outlet 24 for withdrawing a $CO_2$ depleted gas 26, and a liquid outlet 28 for withdrawing an ion enriched solution 30. The rotating reactor 14 can also include a rotation mechanism 32 including a motor 36 and a drive shaft 34 operatively connecting the motor to the reaction chamber for providing the torque for rotating the reaction chamber around a rotational axis.

The ion enriched solution 30 can then be supplied to a regeneration unit 38 for regenerating the solution by desorption or mineralisation, to produce a regenerated solution 40. In the case of desorption, a $CO_2$ enriched gas stream 42 is produced, whereas in the case of mineralization a solid mineral stream (e.g., solid carbonates) is produced. The regenerated solution 40 can then be recycled in whole or in part to the absorption stage, which in FIG. 1 includes the rotating reactor 14. The regeneration unit can have various constructions and may take the form of various types of reactors, such as a conventional packed column or a high intensity reactor, such as a rotating packed bed (RPB). Carbonic anhydrase may be present in the desorption unit, for example immobilized with respect to internals of the desorption unit or micro-particles flowing with the ion rich solution, or free in the solution. The high intensity desorption unit can be operated in conjunction with the high intensity absorption reactor such that the temperature, pressure, pH, and solvent concentration conditions do not substantially denature the carbonic anhydrase.

Figure 4:
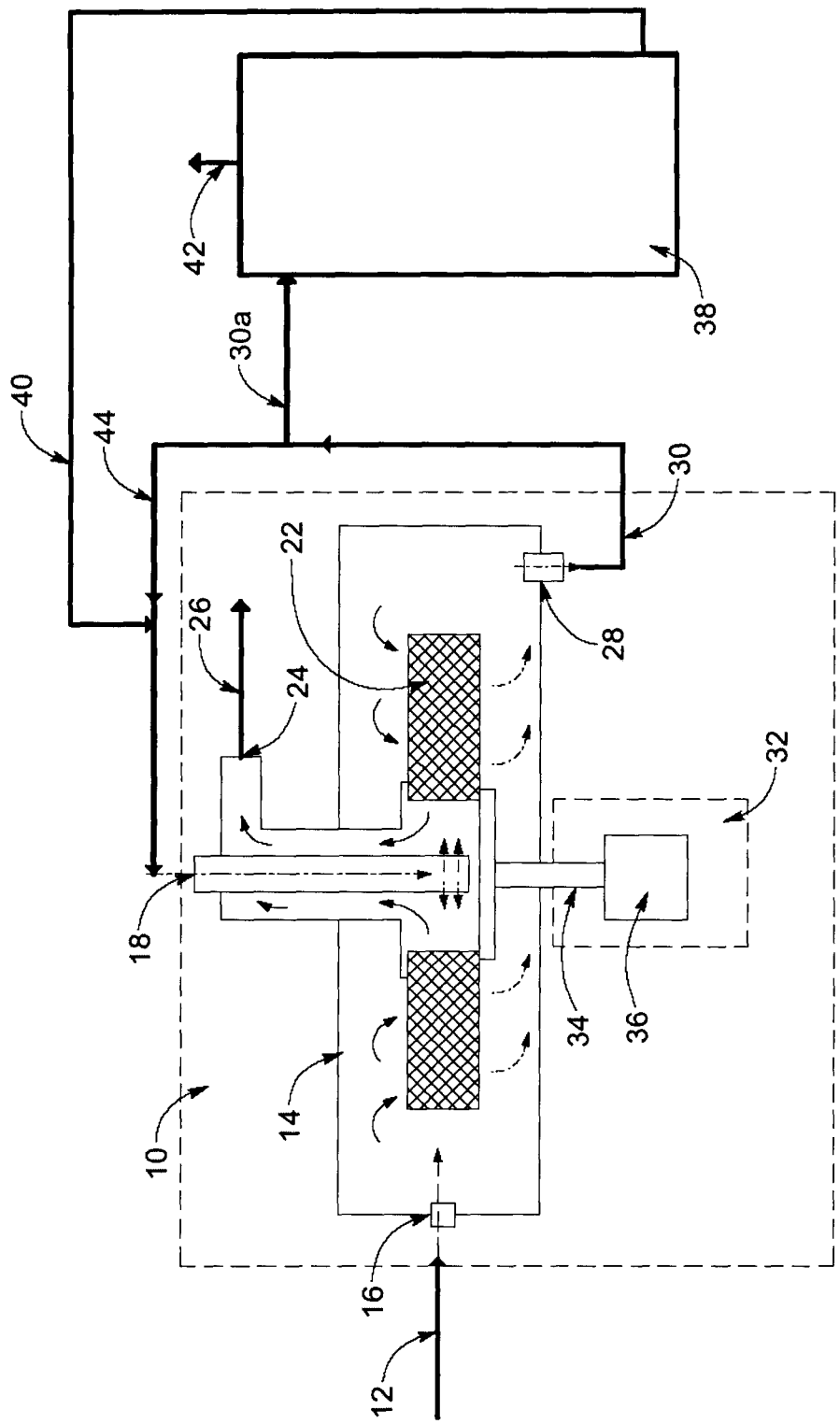
FIG. 4 is a schematic representation of a second absorption and desorption system including a rotating packed bed absorber.

Another possible process configuration is shown in FIG. 4. According to this configuration, the ion enriched solution 30 is divided in two streams (30a and 44). Stream 30a is supplied to a regeneration unit 38 for regenerating the solution by desorption or mineralisation as described above and stream 44 is sent back to the high intensity reactor. In the case the solution is fed to a regeneration unit, the regenerated solution 40 is sent back to the rotating contactor where it is combined with stream 44 (which is part of the recirculating loop around the RPB), prior to being fed back to the biocatalytic unit 10. The $CO_2$ loading of steam 20 depends on the $CO_2$ loading of stream 40 and on the ratio of the flowrates of stream 44 to 40. For example, the ratio of the flowrates of stream 44 to stream 40 can be between 0/1 and 10/1, 1/10 and 5/1, 1/2 and 2/1 or 3/4 and 4/3, for example. The flowrate ratios can also change and can be controlled during operating in order to favour certain process conditions. In some scenarios, the composition of certain streams (e.g., ion enriched solution 30, absorption solution 20, and/or streams 40, 44/30a, etc.) can be monitored and the flowrate ratio can be modified depending on the compositions in order to effect greater regeneration or recycle more ion enriched solution directly back into the absorption reactor. In some implementations, the stream 30 is split such that more solution is sent to desorption than is recycled back without desorption. In addition, the step of splitting the stream 30 can produce two or more streams each having substantially similar compositions, although stream 30 can be separated so that the two streams have different compositions, e.g., stream 44 or 30a could have higher enzyme concentration or one of the streams may contain no enzyme. In some scenarios, the stream 30 can be split into more than two streams, and each of the resulting streams can be supplied to a different unit of the overall process, e.g., regeneration unit, heat exchanger, solids separator, back to one or more high intensity absorbers that are in series or parallel, and so on, and the flowrate ratios of the various streams can be controlled based on desired process parameters.

Figure 5:
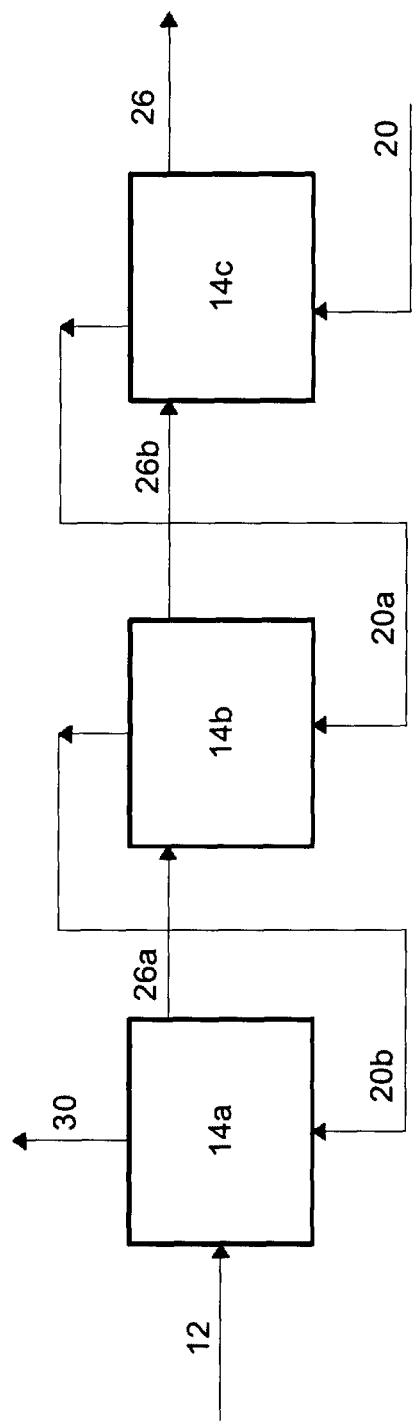
FIG. 5 is a schematic representation of a system where multiple high intensity contactors can be used in series for $CO_2$ absorption.

In another process configuration where $CO_2$ absorption is achieved by operating multiple rotating contactors in series and counter-currently, as illustrated in FIG. 5, the $CO_2$ containing gas 12 can be fed to a first rotating contactor 14a to contact the absorption solution 20b. The treated gas 26a, exiting from the first contactor 14a, is then fed to a second contactor 14b and the gas exiting the second contactor 26b is then fed to a third contactor 14c. In a similar manner, the absorption solution 20 is fed to the third rotating contactor 14c and the solution 20a exiting the third rotating contactor 14c is then fed to the second contactor 14b, to further remove $CO_2$ from the gas 26a and the absorption solution expelled from the second rotating contactor 20b is then sent to the first rotating contactor 14a. The treated gas 26 can then be sent out to the atmosphere whereas the $CO_2$ rich absorption solution 30 can be sent to the regeneration unit 38 as shown, for example, in FIG. 1. An alternative arrangement to the one illustrated in FIG. 5 is that the gas and liquid streams are fed co-currently such that the liquid stream with the highest ion content is contacted with the gas stream with the highest $CO_2$ content, and the liquid stream with the liquid stream with the lowest ion content is contacted with the gas stream with the lowest $CO_2$ content.

Figure 6:
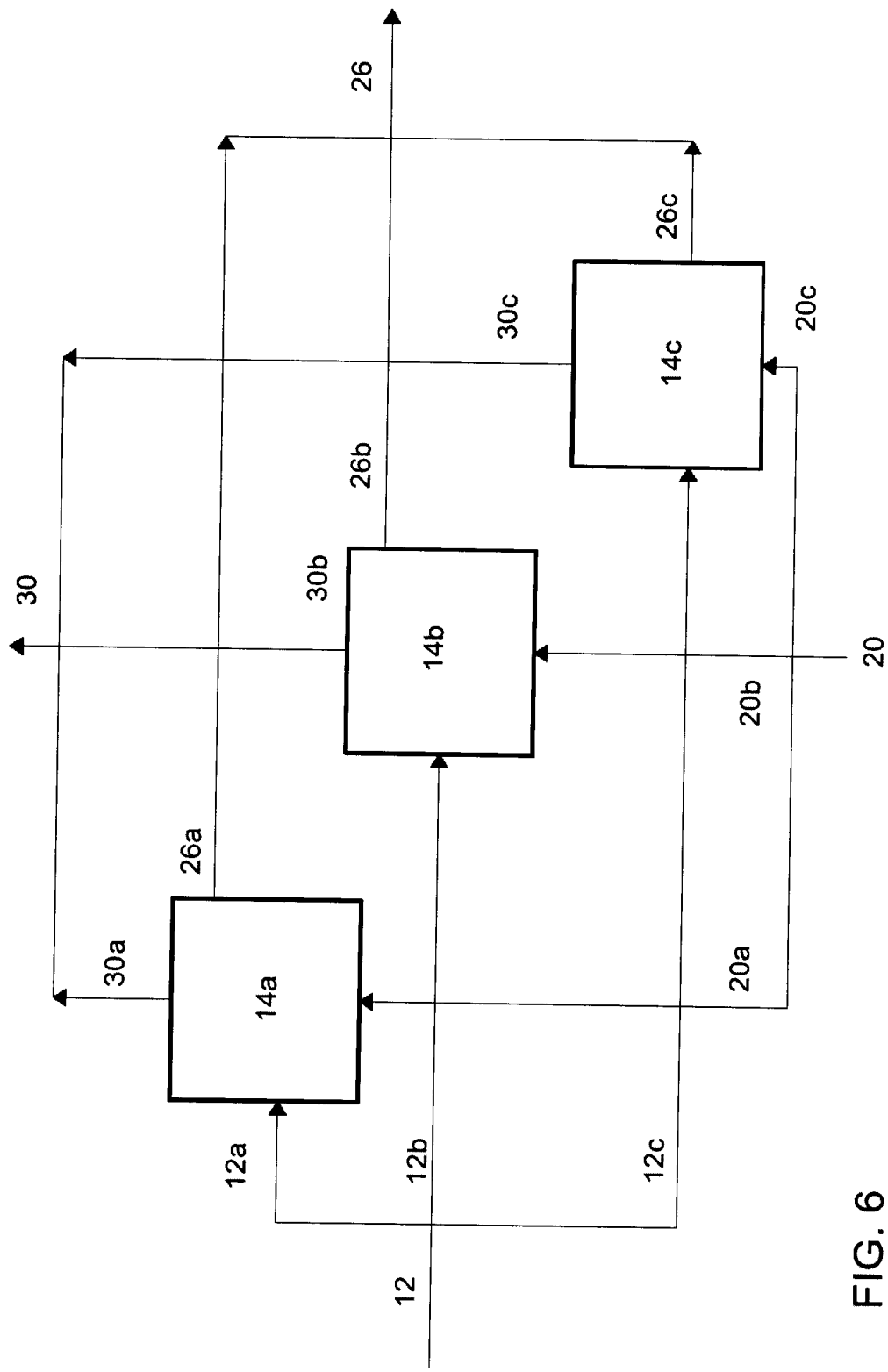
FIG. 6 is a schematic representation of a system where multiple high intensity contactors are used in parallel to remove $CO_2$ from a $CO_2$ containing gas.

In another configuration where $CO_2$ absorption is achieved by operating multiple rotating contactors in parallel with a counter-current operation, as illustrated in FIG. 6, the $CO_2$ containing gas 12 is split into three gas streams 12a, 12b and 12c which are respectively fed to multiple (e.g., three) rotating contactors 14a, 14b and 14c. In a similar manner, the absorption solution stream 20 is split into multiple (e.g., three) liquid streams 20a, 20b and 20c and are respectively fed to the rotating contactors 14a, 14b and 14c. In each of the three rotating contactors the absorption solution contacts the $CO_2$ containing gas and absorbs $CO_2$. The treated gas streams 26a, 26b and 26c are then released out of the process. The $CO_2$ rich absorption solutions 30a, 30b and 30c are then sent to a regeneration unit 38 as shown, for example, in FIG. 1. The streams 30a, 30b and 30c can be combined (30) prior to being fed to the regeneration unit. In an optional configuration, the entire gas flow would be fed to the first contactor 14a, and then the gas outlet would be fed to the second contactor 14b and then to the third contactor 14c. So the gas would flow though the units in series. In this optional configuration, the liquid flow would be split and fed to the units in parallel as described previously. In an additional optional configuration, the gas could be fed to the units in parallel and the liquid would flow through the units in series.

Figure 7:
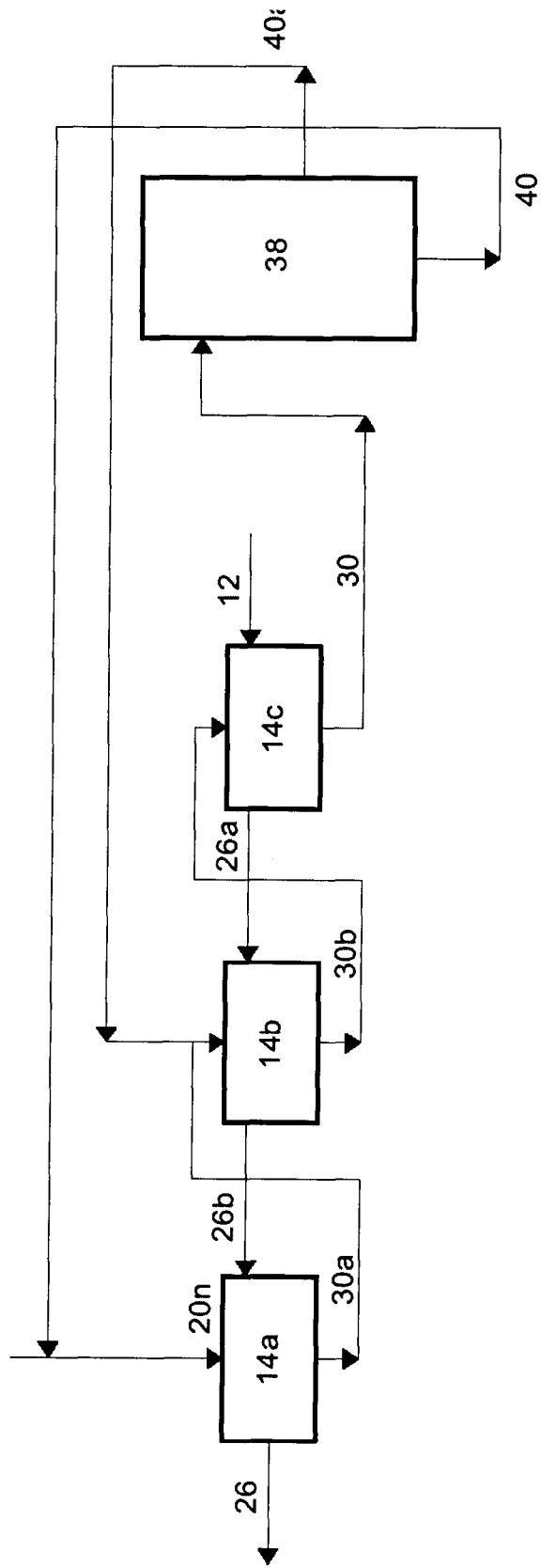
FIG. 7 is a schematic representation of an absorption/desorption system where multiple high intensity contactors are used in series and where a stream of semi-lean liquid phase is sent back to one of the high intensity contactors.

In a configuration where multiple rotating contactors in series are used to remove $CO_2$ from a $CO_2$ containing gas 12 as shown in FIG. 7, a process variation is that a stream of partly regenerated absorption solution 40a is sent back to at least one of the rotating contactors. This recycle can be done for one or more of any of the contactors.

Techniques described herein can facilitate increasing the impact of biocatalysts in a gas absorption process. For instance, in operations where a liquid phase is contacted with a gas phase to absorb a component of interest, biocatalysts may be provided free or immobilized on particles that are carried with the liquid phase. In order to increase the kinetic impact of the biocatalyst, the contact between the gas phase and the liquid phase (containing the biocatalyst) takes place in a high intensity gas-liquid contactor to intensify the mass transfer of the gaseous component of interest toward the liquid phase, employing process intensification principles. A significant option for intensifying the mass transfer in a gas-liquid contactor is to use a rotating contactor, which may include a cyclone/vortex or a rotor, under enhanced acceleration conditions. This enhanced acceleration facilitates formation of thinner films, smaller bubbles and droplets, and increased flooding velocities for counter-current systems. In some implementations, the enhanced acceleration can result in an increase in the gas-liquid mass transfer by a factor of 10 to 100 compared to conventional techniques.

Intensification Reactors and Techniques

Various types of intensification techniques may be used in conjunction with carbonic anhydrase for enhanced $CO_2$ capture. The techniques can include intensification equipment and/or intensification methods. Rotating reactors, such as rotating packed beds, rotating disc contactors, rotating zigzag bed reactors, multi-rotor zigzag rotating contactor and/or rotating contactor with split packing can be used. In addition, other types of high intensity reactors can be used in connection with some implementations of the techniques described herein, such as gas-liquid jet reactors, swirling gas-liquid contactors, or contactors as described in US patent application published as No. 2010/0320294.

Process intensification techniques typically rely on the intensification of various different process parameters with a view of accelerating the process and reducing the size of equipment required for unit operations. Some potential intensification parameters, such as elevated pressures and temperatures, have been leveraged to accelerate unit operations by enhancing the kinetics of various mass transfer and reaction phenomena in the process. However, the intensification of some process parameters can lead to detrimental effects on some biocatalytic processes that employ biocatalysts that can denature at elevated temperature conditions for example. Nevertheless, some process intensification techniques focus on "fluid dynamic" intensification parameters, such as reducing the liquid film thickness flowing over packing material by leveraging rotational force to drive the liquid instead of reliance on gravitational force. Contactors that leverage fluid dynamic intensification parameters can therefore increase mass transfer rates to take advantage of biocatalytic reaction kinetics while avoiding detrimentally impacting the biocatalysts. In this regard, the term "high intensity" reactor or "high intensity" contactor used herein refers to units that leverage fluid dynamic intensification parameters, rather than parameters such as high temperature that could have detrimental effects on the biocatalyst, to enhance mass transfer rates.

Referring to FIGS. 1, 2, 3 and 4, a Higee (or high gravity) rotating contactor 14 may include rotating discs, rotating packing or rotating zigzag bed. The rotating disc contactor is also known as a spinning disc contactor, and the rotating packed contactor is also known as a Higee contactor or rotating packed bed (RPB). Various different configurations and constructions of rotating discs or RPBs, can be used. For both high intensity contactor types, the method includes feeding a gas phase, containing a gas species of interest to absorb, to the contactor. The gas phase is fed via an outer part of the contactor. The liquid phase that will absorb the gaseous species of interest is fed via an inner part of the contactor. Because of the centrifugal force coming from the rotation of the reaction chamber housing the packing or the discs, the liquid will flow outwardly through the packing or form a film on the surface of the discs or of the zigzag bed. The rotational speed can be adjusted to generate an important centrifugal force of several "g" in such a way as to minimize the liquid film thickness and maximize the contact surface area between the gas and the liquid phases, to enhance removal of the gas species of interest.

Regarding high intensity reactors that have discs, packing material or zigzag bed, the process may be operated using biocatalytic particles that flow with the solution through the reactor and/or the process may be operated such that bicarbonate precipitates form in the solution and are carried out of the reactor. In scenarios where the particles and/or precipitates are nanosized, the reactor may be an RPB or a spinning disc reactor. In scenarios where the particles and/or precipitates are micron sized or larger, a spinning disc reactor may be preferred for handling such larger solid particulates.

Regarding high intensity reactors that have packing material provided in the reaction chamber(s), the packing that is used can have certain characteristics to benefit the mass transfer and biocatalytic impact on $CO_2$ absorption. In some implementations, the packing material can be a reticulated packing material, which can be composed of metal for example. The reticulated packing material can have large surface area per unit volume and/or enable high voidage characteristics. For example, the specific surface area of the packing material can be between about 500 $ft^2/ft^3$ to about 1000 $ft^2/ft^3$, optionally between about 700 $ft^2/ft^3$ to about 800 $ft^2/ft^3$, still optionally about 750 $ft^2/ft^3$. The voidage of the packing material can be above about 80%, above about 85%, above about 90%, or between about 85% and about 95%, for example. Other examples of packing are composite layers of gauze or expanded metal, wound layers of fibrous material, or structured and random packing commonly used in a packed column.

Some combinations of carbonic anhydrase biocatalyst, with absorption compounds of interest, for $CO_2$ absorption in a packed column as part of a $CO_2$ capture process have resulted in $CO_2$ capture rates, installation footprint and energy requirement comparable to conventional chemical solvent based processes. Some advantages of such enzyme enhanced processes is that the solutions being used (e.g., carbonate based solutions) are less reactive than conventional primary alkanolamines, more stable, and present less environmental issues. One finding with respect to the impact of the carbonic anhydrase enzyme in processes based on the use of a packed column as an absorber, is that the enzyme impact appears to be limited by the $CO_2$ mass transfer rate provided in this conventional absorber type. Therefore, fluid dynamic intensification techniques combined with carbonic anhydrase can enhance the impact of the enzyme on the $CO_2$ capture system and thus further benefit from both the intensification and biocatalytic effects.

Absorption Solutions and Compounds

In some implementations, the techniques can generally include removing a selected gas component from a gas phase, using a liquid phase that is contacted with the gas phase. The contact between the gas and the liquid will result in the absorption of the selected gas component by the liquid phase. This liquid phase can be selected and formulated based on its ability to absorb and store the absorbed selected gas component, and may therefore include one or more absorption compounds. The liquid phase composition can be formulated specifically to efficiently absorb the gas component of interest. The liquid phase may include water and other absorption compounds species that will absorb and react with the absorbed gaseous species. The liquid can also include other compounds such as de-foaming compounds. In some cases, the liquid phase can also contain the biocatalysts which are carried with the liquid through the reactor.

In some implementations, the absorption solution can be formulated to include one or more absorption compounds in addition to water to facilitate $CO_2$ absorption. In some implementations, the absorption compound can have a slow reaction rate with $CO_2$, but provide high cyclic capacity, no carbamate formation and/or lower energy requirement for their regeneration as compared to primary alkanolamines commonly used in post-combustion $CO_2$ capture process and/or enable the use of low grade heat available on the implementation site since regeneration conditions are at temperature and pressure conditions enabling such low grade heat utilization. "Low-grade heat" should be understood to include low- and mid-temperature heat that cannot be converted efficiently by conventional methods. The particular thermal conditions of low-grade heat or industrial waste heat are industry dependent For example, the low-grade heat can be waste heat from a process stream that is at a temperature level below about 1000; in the food and beverage industry the low-grade heat temperature level can be about 80° C. Low-grade heat can be provided by a heat transfer fluid having a temperature below 100° C., below 90° C., below 80° C., be low 70° C. or below 60° C., or between any two of the aforementioned values. The heat transfer fluid may include water, heat transfer oils, freon or phase-changing fluids, for example. The absorption compounds of interest can include, for example, slow reactive compounds. In some implementations, the absorption compound includes tertiary amines, tertiary alkanolamines, tertiary amino-acids, tertiary amino-acid salts, carbonates or a mixture thereof.

In some implementations, the biocatalyst is used in conjunction with an absorption compound which may include primary, secondary and/or tertiary amines (including alkanolamines); primary, secondary and/or tertiary amino acids; and/or carbonates. The absorption compound may more particularly include amines (e.g. piperidine, piperazine and derivatives thereof which are substituted by at least one alkanol group), alkanolamines (e.g. monoethanolamine (MEA), 2-amino-2-methyl-i-propanol (AMP), 2-(2-amino-ethylamino)ethanol (AEE), 2-amino-2-hydroxymethyl-i,3-propanediol (Tris), N-methyldiethanolamine (MDEA), dimethylmonoethanolamine (DMMEA), diethylmonoethanolamine (DEMEA), triisopropanolamine (TIPA) and triethanolamine), dialkylether of polyalkylene glycols (e.g. dialkylether or dimethylether of polyethylene glycol); amino acids which may include potassium or sodium salts of amino acids, glycine, proline, arginine, histidine, lysine, aspartic acid, glutamic acid, methionine, serine, threonine, glutamine, cysteine, asparagine, leucine, isoleucine, alanine, valine, tyrosine, tryptophan, phenylalanine, and derivatives such as taurine, N,cyclohexyl 1,3-propanediamine, N secondary butyl glycine, N-methyl N-secondary butyl glycine, diethylglycine, dimethylglycine, sarcosine, methyl taurine, methyl-a-aminopropionic acid, N-(β-ethoxy)taurine, N-(β-aminoethyl)taurine, N-methyl alanine, 6-aminohexanoic acid; and which may include potassium carbonate, sodium carbonate, ammonium carbonate, promoted potassium carbonate solutions and promoted sodium carbonate solutions or promoted ammonium carbonates; or mixtures thereof. Absorption compounds can be added to the solution to aid in the $CO_2$ absorption and to combine with the catalytic effects of the carbonic anhydrase.

Biocatalysts and Delivery Methods

The biocatalysts considered for $CO_2$ capture operations is the enzyme carbonic anhydrase. This enzyme is one of the fastest known enzymes, and catalyses the interconversion of $CO_2$ and bicarbonate according to the following reaction:

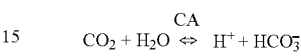

Carbonic anhydrase is not just a single enzyme form, but includes a broad group of metalloproteins that exists in genetically unrelated families of isoforms, α, β, γ, δ and ε. Different classes, isoforms and variants of carbonic anhydrase have been used in order to catalyze the hydration reaction of $CO_2$ into bicarbonate and hydrogen ions and the bicarbonate dehydration reaction into $CO_2$ and water. Under optimum conditions, the catalyzed turnover rate of the hydration reaction can reach $1 \times 10^6$ molecules/second.

In some implementations, the biocatalyst can be immobilized directly onto the surface of the packing material via chemical fixation of the biocatalyst. In some implementations, the biocatalyst or an aggregate of the biocatalysts, such as CLEAs or CLECS, can be used in the high intensity reactor. In some other implementations, particles with the biocatalyst at their surface or entrapped inside the particles can be used.

In terms of particle delivery methods, the biocatalysts can be immobilized or otherwise delivered via particles that are carried with the absorption solution through the reaction chamber. In a conventional packed reactor, there is reliance on gravity as a driving force for establishing the liquid film that flows over the packing material. In the high intensity reactors, the biocatalytic particles may be provided to have a size and concentration in the absorption solution to flow with the liquid and to be smaller than the liquid film flowing on the surfaces of the packing material, which may be reticulated packing material, composite layers of gauze or expanded metal, would layers of fibrous material, structured packing or random packing, as described above. The biocatalytic particles may also have other characteristics to remain distributed in the absorption solution in a generally uniform manner under the rotational force. In some implementations, the density of the biocatalytic particles is provided to be low enough such that the particles are carried with the liquid upon the substantial acceleration of the liquid within the rotating reactor. In addition, the particles can be sized in accordance with the thin liquid film, and may be for example at least an order of magnitude smaller than the thickness of the liquid film.

In some implementations, the biocatalyst can be immobilized with respect to the internals (e.g., packing material, discs, zigzag bed, etc.) in the high intensity reactor. For RPB reactors, the biocatalyst can be immobilized on the packing material using various techniques, such as entrapment, covalent bonding, and so on. In some scenarios, the biocatalyst can be immobilized in an immobilization material that is provided on the packing material as a coating, and may be spray coated onto the packing material. The immobilization material may include polysulfone and/or polysulfone grafted with polyethylene glycol and/or any one or a combination of polymeric materials described in U.S. Pat. No. 7,998,714. The immobilization material may include micellar and/or inverted micellar polymeric materials, such as micellar polysiloxane material and/or micellar modified polysiloxane materials described in PCT patent application No. WO 2012/122404 A2. In some implementations, the immobilization material may include chitosan, polyacrylamide and/or alginate.

In some scenarios, the biocatalyst present in the packed reactor can lose activity over time, and techniques for replenishing activity of the biocatalytic reactor may be employed. Various activity replenishment techniques can be used depending on the type of the reactor and the delivery method of the biocatalyst. Some activity replenishment techniques are described, for example, in U.S. patent application Ser. No. 14/401,609. In the case of smaller sized high intensity reactors, such as RPBs, activity replenishment can be facilitated for various reasons. In some implementations, the packing material including immobilized biocatalysts can be more easily removed and replaced. In some implementations, the packing material can be reactivated in situ within the reaction chamber by supplying one or more biocatalyst activation solution into the reaction chamber to contact the packing material. For example, such in situ reactivation can include a series of solutions to pre-treat, clean, functionalize, etc., and eventually provide the immobilized enzyme onto the packing material. Since the volume of the high intensity reaction chamber is significantly smaller than conventional packed columns, for example, solutions requirements for in situ reactivation can be reduced and reactivation can be generally facilitated.

Biocatalyst can be provided at various concentrations in the high intensity reactor, in part depending on the delivery method of the biocatalyst.

In some scenarios, the biocatalyst is provided free in the absorption solution supplied to the high intensity reactor, at an elevated concentration. In this context, "elevated concentration" means that the concentration of the biocatalyst is greater than the maximum concentration of the same biocatalyst under similar conditions in a conventional reactor, where such maximum concentration corresponds to a plateau of biocatalytic impact on the reaction.

In some scenarios, in the case the absorption solution comprising a carbonate compound, such as sodium or potassium carbonate, the absorption of $CO_2$ by the solution results in a dissolved concentration of bicarbonate ions that is sufficient to cause the precipitation of carbonated solids, such as sodium or potassium bicarbonate. The precipitated solids thus formed can be in suspension in the ion-rich solution expelled from the contactor. In some scenarios, the process is conducted so that the ion enriched solution will be free of precipitates, such as bicarbonate precipitates.

In addition, the biocatalyst can be provided in the high intensity reactor at a concentration (which may be an elevated concentration) that is below an upper concentration limit corresponding to a plateau of biocatalytic impact in the high intensity reactor. At certain high concentrations of biocatalyst there will be a plateau of biocatalytic impact on the hydration reaction. For example, at certain high concentrations of biocatalyst the absorption solution may become more susceptible to foaming and/or may have a high viscosity that would begin to limit mass transfer in the high intensity reactor. By keeping the biocatalyst concentration below such a plateau enables more efficient use of biocatalyst in the system.

In some scenarios, the biocatalyst can be provided at other concentrations depending on various factors, such as operating conditions, biocatalyst delivery method, type of biocatalyst, type of high intensity reactor, type of input gases and liquids, and so on. For example, carbonic anhydrase concentrations can range from 0.5 g/L to 10 g/L, 1 g/L to 8 g/L, 2 g/L to 6 g/L, or 3 g/L to 5 g/L, or from 0.1 g/L to 10 g/L, 0.2 g/L to 8 g/L, 0.5 g/L to 6 g/L, or 1 g/L to 5 g/L. In addition, the biocatalyst concentration can be maintained to be relatively constant, or may be modified over time which may be accomplished by in-line addition of biocatalyst to the absorption solution.

Process Additives and Operation

In some implementations, the absorption solution can include additives that may be in addition to one or more absorption compounds and/or biocatalysts. In some scenarios, the additives can include a "defoamer". In the present application, the term "defoamer" includes foam-reducer compounds that reduce foam once it is formed and/or anti-foam compounds that inhibit foam formation. Defoamers can be used in various scenarios where the biocatalyst and/or the process operating conditions are such that the absorption solution tends to have foam production. The presence of foam can negatively affect gas-liquid mass transfer and therefore can reduce performance of the $CO_2$ absorption. For example, higher concentrations of biocatalyst (e.g., carbonic anhydrase) can increase the tendency of foam production, which was observed during experiments. In some scenarios, both foam-reducer compounds and anti-foam compounds are used in conjunction with systems or processes as described herein.

Various different types of defoamers can be used, depending on the given application of the process and operating conditions. The anti-foam or foam-reducer may comprise oil, hydrophobic solid particles or a mixture of both. Non-polar oils (mineral oils, silicone oils) and polar oils (fatty alcohols and acids, alkylamines, alkylamides, tributyl phosphate, tioethers) can be used. The solid particles could be inorganic (silica, $AL_2O_3$, $TiO_2$), wax or polymeric. The defoamer (i.e., anti-foam or foam-reducer) compound can include an oil-in-water emulsion, water-in-oil emulsion, polyol based compounds which may be in the form of a polyol based dispersion, silicon based compounds which may be in the form of a non-ionic silicon emulsion, or silica particle suspension, or a combination thereof.

The defoamer can be provided in various concentrations, for example a concentration of at least 10 mg/L or at least 50 mg/L based on the volume of the absorption solution, a concentration of at least 200 mg/L based on the volume of the absorption solution. Or a concentration of between 50 and 300 mg/L or between 100 and 300 mg/L, based on the volume of the absorption solution.

In addition, the high intensity reactor can be operated such that the intensification includes subjecting the fluids to high forces, e.g., high centrifugal forces, which are provided above certain thresholds for an enhanced biocatalytic process. For example, in a rotating high intensity reactor (e.g., RPB) the centrifugal force can be provided above a threshold relative to gravity (g). This can be reflected by the centrifugal acceleration as per the following equation:

$$A_c = V^2 R$$

where $A_c$ is centrifugal acceleration, V is the rotational velocity, and R is the relevant radius.

For example, in an RPB having a radius of 0.15 m, operated at 1200 RPM (120 rad/s), the centrifugal acceleration is 2381 m/s$^2$ (243 g) Operating at 450 RPM would provide a centrifugal acceleration of about 303 m/s$^2$ (31 g).

In some implementations, the high intensity reactor is operated to provide acceleration conditions of at least 25 m/s$^2$, 50 m/s$^2$, 100 m/s$^2$, 150 m/s$^2$, 200 m/s$^2$, 250 m/s$^2$, 300 m/s$^2$, 350 m/s$^2$, 400 m/s$^2$, 450 m/s$^2$, 500 m/s$^2$, 600 m/s$^2$, 700 m/s$^2$, 800 m/s$^2$, 900 m/s$^2$, 1000 m/s$^2$, 1500 m/s$^2$, 2000 m/s$^2$, 2500 m/s$^2$, or 3000 m/s$^2$, or acceleration conditions between any two of the above values or other values disclosed herein. Furthermore, due to the proportional relation of $A_c$ to $V^2$, the rotational velocity can be adjusted to provide a significant impact on the acceleration and corresponding impact on the hydrodynamics of the system to enhance biocatalytic effects.

It should also be noted that various aspects of the processes and/or systems for removing $CO_2$ from a gas can also be applied to the removal of a gas component from a mixed gas stream and employing a catalyst (e.g., biocatalyst such as an enzyme) in a high intensity reactor. Examples, aspects and implementations described herein for $CO_2$ capture and using carbonic anhydrase can be adapted using, for example, other biocatalysts having high turnover rates for a given reaction in order to covert a dissolved gas component into an ionic compound in the absorption solution.

Examples & Experimentation

Experimentation Series 1

A $CO_2$ absorption test series was conducted using a carbonic anhydrase as a biocatalyst in combination with a 1 M potassium carbonate solution ($K_2CO_3$); the lean $CO_2$ loading of the solution was 0.81 mol carbon/mol potassium ions. An antifoam agent, AF-204 (Sigma Aldrich) which is a polyol-based dispersion, was added to the carbonate solution at a concentration of 200 mg/L. The $CO_2$ concentration in the gas phase was 8% (v/v) dry basis. The absorber consists in a packed column containing 16 mm polypropylene Pall rings as a packing to provide the gas/liquid contact surface area. The column has a diameter of 0.175 m and a height of 6.85 m. The L/G ratio was 7 (w/w). Tests were conducted at 30° C. temperature. The impact of carbonic anhydrase on the $CO_2$ transfer rates was evaluated at 4 different enzyme concentrations.

Figure 8:
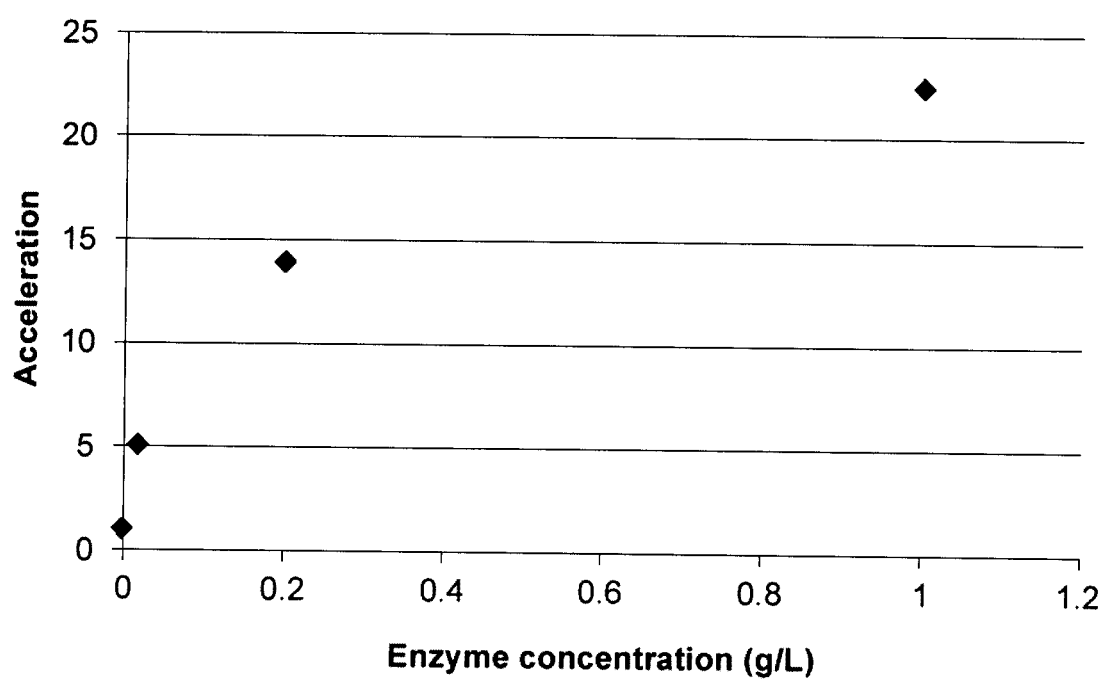
FIG. 8 is a graph of Acceleration of the $CO_2$ absorption rates in a packed column using a 1M $K_2CO_3$ absorption solution in combination with 4 different carbonic anhydrase concentrations.

Results reported in FIG. 8 show that increasing the enzyme concentration translates into an acceleration of the $CO_2$ mass transfer rate. However, the impact of the enzyme is greater at lower concentration. This seems to indicate that the $CO_2$ mass transfer from the gas phase to the liquid phase may be limiting the enzyme impact at higher enzyme concentration.

Experimentation Series 2

Another $CO_2$ absorption test series was conducted using a carbonic anhydrase as a biocatalyst in combination with a 1.45M potassium carbonate solution ($K_2CO_3$); the lean $CO_2$ loading of the solution was 0.73 mol carbon/mol potassium ions. An antifoam agent, AF-204 (Sigma Aldrich) which is a polyol-based dispersion, was added to the carbonate solution at a concentration of 200 mg/L. The $CO_2$ concentration in the gas phase was 10% (v/v) dry basis. The absorber consists in a packed column containing 4.57 m of Metal Mellapak M250Y packing and 3.05 m IMTP Metal 25 packing for a total packing height of 7.62 m. The column has a diameter of 0.254 m. The L/G ratio was 10 (w/w). Tests were conducted at a 30° C. temperature. The impact of carbonic anhydrase on the $CO_2$ capture efficiency was evaluated at 4 different enzyme concentrations.

Figure 9:
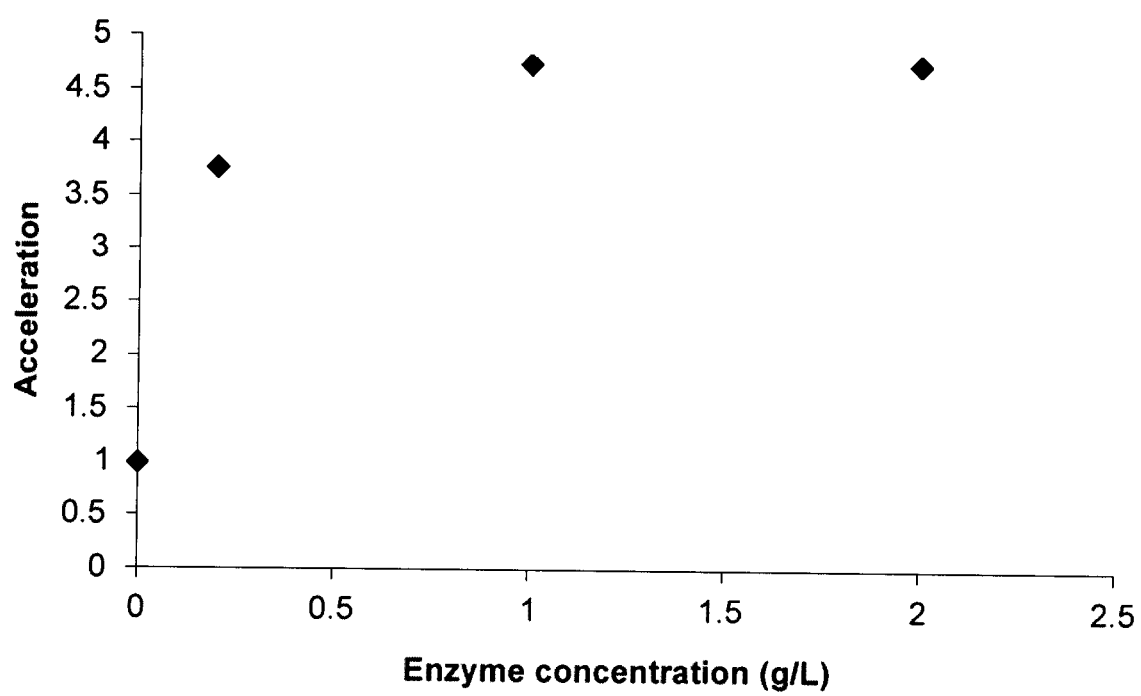
FIG. 9 is a graph of Acceleration of the $CO_2$ absorption rates in a packed column using a 1.45M $K_2CO_3$ absorption solution in combination with 4 different carbonic anhydrase concentrations.
Figure 10:
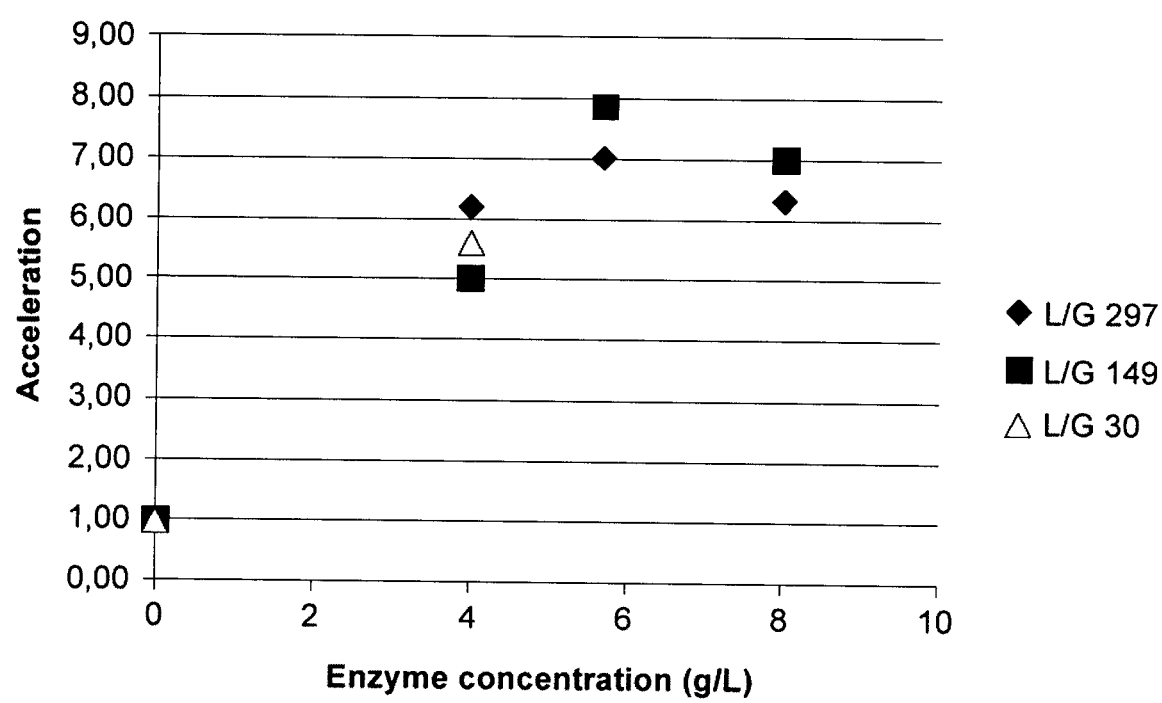
FIG. 10 is a graph of Acceleration of the $CO_2$ absorption rates in a rotating packed bed using a 1.45 M $K_2CO_3$ in combination with 3 different enzyme concentrations at L/G of 30, 149 and 297 (w/w). The rotational speed of the contactor is 450 rpm.

Results are reported in FIG. 9. Data show that increasing the enzyme concentration translates into an acceleration of the $CO_2$ mass transfer for enzyme concentration up to 1 g/L. This clearly indicates that the $CO_2$ mass transfer from the gas phase to the liquid phase is limiting the enzyme impact at enzyme concentrations around 1 g/L and higher.

Experimentation Series 3

Figure 11:
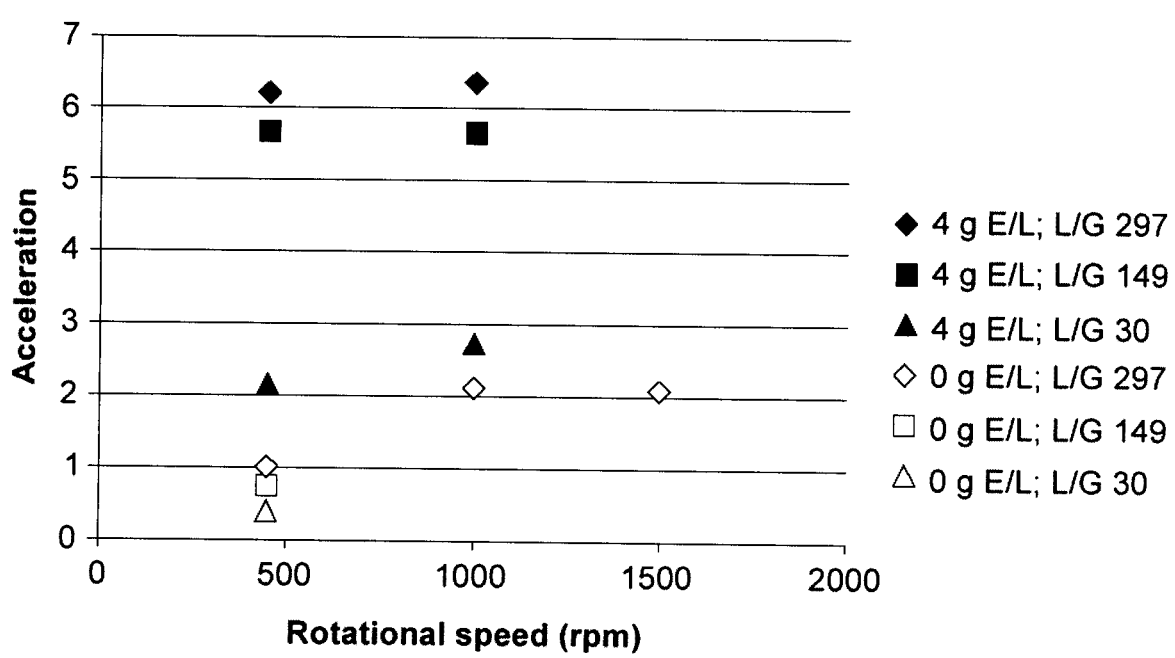
FIG. 11 is a graph showing Acceleration of the $CO_2$ absorption rates in a rotating packed bed using a 1.45 M $K_2CO_3$ at an enzyme concentration of 0 and 4 g/L, for L/G of 30, 149 and 297 (w/w) and rotational speed of the contactor of 450, 1000 and 1500 rpm.
Figure 12:
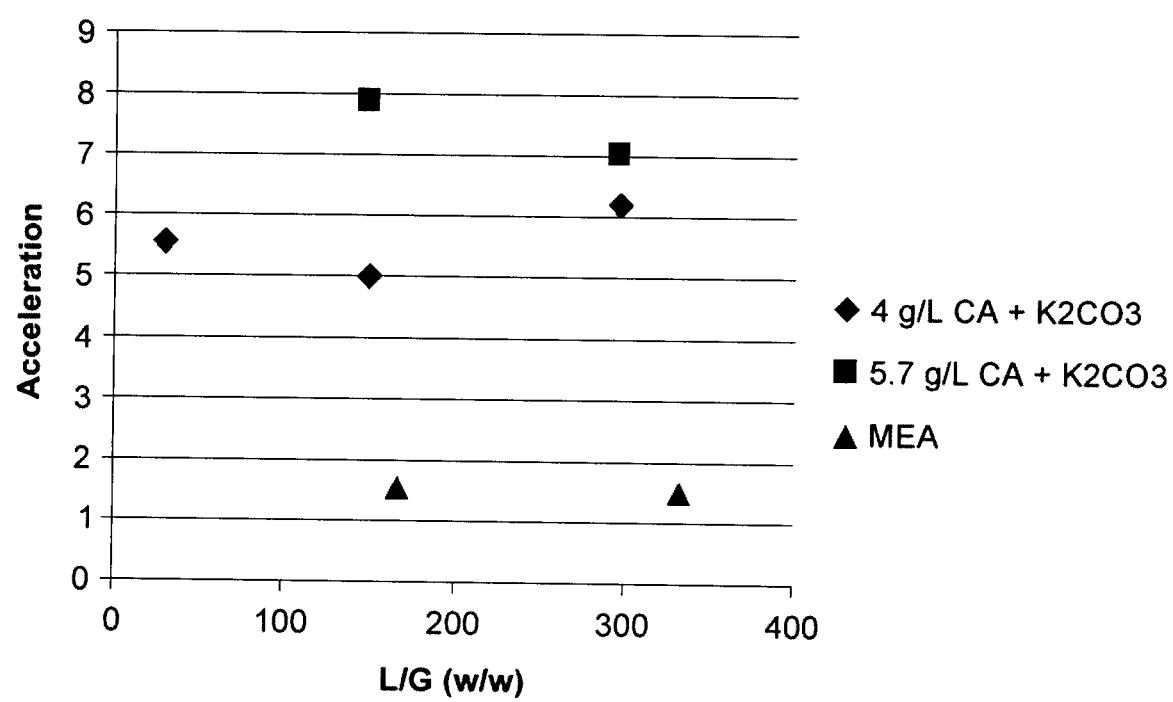
FIG. 12 is a graph showing a comparison of the $CO_2$ absorption performance obtained using a 5M MEA solution (lean $CO_2$ loading of 0.28 mol C/mol MEA) and using a 1.45 M $K_2CO_3$ solution (lean $CO_2$ loading of 0.62 mol C/mol potassium ions) containing 4 or 5.7 g/L of carbonic anhydrase enzyme for different L/G. The rotational speed of the contactor is 450 rpm.

$CO_2$ absorption tests were conducted using a carbonic anhydrase as a biocatalyst in combination with a 1.45M potassium carbonate solution ($K_2CO_3$) in a rotating packed bed; the $CO_2$ loading of the solution was adjusted to 0.62 mol carbon/mol potassium ions. An antifoam agent, AF-204 (Sigma Aldrich) which is a polyol-based dispersion, was added to the carbonate solution at a concentration of 200 mg/L. The $CO_2$ concentration in the gas phase was 9.5% (v/v) dry basis. The packing consisted of steel foam with 90% porosity. The dimensions of the packing are the following: height 2.54 cm, outer diameter: 29.85 cm and inner diameter: 8.89 cm. The L/G ratios were 30, 149 and 297 (w/w). Tests were conducted at room temperature for 4 enzyme concentrations. The packed bed rotational speed was adjusted at 450 rpm. Results are shown in FIG. 12. It can be observed that for this absorber configuration, the increase of the enzyme concentration results in an increase in the acceleration of the $CO_2$ capture rate as compared to a solution without enzyme up to an enzyme concentration value close to 5.6 g/L. The observed decrease in performance observed for an enzyme concentration of 8 g/L was correlated to the presence of foam in the system. Under these particular conditions, the anti-foam concentration was not sufficient to avoid solution foaming. As a consequence of the presence of foam, the mass transfer rate was decreased as the gas/liquid surface was decrease because of the presence of foam. Moreover, a comparison with results presented in FIG. 11, shows that a rotating packed bed reactor enables an increase in the $CO_2$ mass transfer rate as compared to a packed column as the impact of enzyme is still significant for concentration of enzymes higher than 1 g/L, value where mass transfer becomes limiting in a packed column.

Experimentation Series 4

Additional tests were performed in the same unit as described in Experimentation series 3. For these tests, a 1.45 M potassium carbonate solution ($K_2CO_3$) having a $CO_2$ loading adjusted to 0.62 mol carbon/mol potassium ions was used. An antifoam agent, AF-204 (Sigma Aldrich) which is a polyol-based dispersion, was added to the carbonate solution at a concentration of 200 mg/L. The tests included measuring the $CO_2$ absorption rate, at different rotational speeds (450, 1000 and 1500 rpm) of the RPB, and at different L/G ratios (30, 149 and 297 (w/w)). Two solutions were tested, the first solution did not contain enzyme whereas the second had an enzyme concentration of 4 g/L. Results are shown in FIG. 11.

Regarding the results obtained for the solution not containing enzyme, it can be observed that the $CO_2$ absorption rate increases with the rotational speed up to 1000 rpm for an L/G of 297 (w/w) and then the Acceleration stays at a plateau. However, for the 4 g/L enzyme solution, the rotational speed has an impact at lower L/G whereas at higher L/G ratios the maximum $CO_2$ absorption rate at the tested process conditions is already reached at 450 rpm. This indicates that the optimal rotational speed depends on the L/G of the system and also on the presence of the enzyme. Acceleration is reported as the $CO_2$ absorption rate divided by the $CO_2$ absorption rate obtained for the solution not containing the enzyme at L/G 297 (w/w) and a rotational speed of 450 rpm.

Experimentation Series 5

In order to compare the performance of the rotating packed bed to the performance obtained in the packed columns described in Examples 1 and 2, specific $CO_2$ absorption rates per unit packing volume were calculated for each system. RPB performance considered for comparison was obtained at an enzyme concentration of 4 g/L, rotational speed of 450 rpm and a L/G of 296 (w/w). Results are shown in Table 1.

TABLE 1

Ratio of the performance of RPB vs. packed columns

| | Specific $CO_2$ absorption rates $\frac{(mg\ CO_2\ m^{-3}s^{-1})_{RPB}}{(mgCO_2m^{-3}s^{-1})_{PaCo}}$ |
|---|---|
| RPB/packed column (Example 1) | 54000/2400 = 22 |
| RPB/packed column (Example 2) | 98000/5000 = 20 |

These data clearly show that using a rotating packed bed increases mass transfer intensity as the absorption rates are 20 times higher than in a packed column for a same volume of packing. It is a clear indication that there is a synergy in using CA containing absorption solution with a rotating packed bed for $CO_2$ capture.

Experimentation Series 6

For the sake of comparison and benchmarking, the performance obtained using carbonic anhydrase in combination with a potassium carbonate solution, 5M MEA solutions were also tested in the rotating packed bed described in Experimentation series 3 under the same L/G. Tests were conducted at 40° C. The $CO_2$ loading of the MEA solution was adjusted to 0.28 mol C/mol MEA, which is typical of values encountered in industrial MEA-based $CO_2$ capture processes. Results are shown in FIG. 12 together with some of the data previously report on FIG. 11. Acceleration values are calculated as the ratio of the $CO_2$ absorption efficiency of a given solution to the $CO_2$ capture efficiency observed with a 1.45 M $K_2CO_3$ solution at a lean $CO_2$ loading of 0.62 mol C/mol potassium ions under same L/G conditions and at room temperature.

It can be first surprisingly observed that MEA absorption rates under the tests conditions are only 1.5× higher than the corresponding absorption rates obtained in a 1.45 M $K_2CO_3$ (loading 0.62 mol/mol) at room temperature. A second surprising observation is that the addition of carbonic anhydrase to the potassium carbonate solution leads to a significant increase in the acceleration of $CO_2$ absorption rates, the increase being more important when the enzyme concentration is higher. The acceleration is about 3.5× more important using 4 g/L enzyme and 5× more important using 5.7 g/L enzyme. These results were surprising notably since previous work using a packed column indicated that the packed column height should be higher when the enzyme was used in combination with potassium carbonate as compared to a MEA-based system for a same $CO_2$ capture efficiency as the L/G for the absorber. This demonstrates that a rotating packed bed, a high intensity contactor, enables enhanced impact of carbonic anhydrase in the $CO_2$ absorption process. This also clearly indicates that using carbonic anhydrase in combination with an absorption solution of interest (as described above) in a rotating packed bed is an advantageous option to reduce equipment size, installation footprint and process energy requirements in $CO_2$ absorption processes.

Some of the advantages related to process intensification of biocatalytically enhanced absorption operations over conventional technology can include equipment size reduction, higher kinetics, capital cost reduction, raw material cost reduction, increased process flexibility and maintenance, and enhanced environmental impact.

Experimentation Series 7

Figure 13:
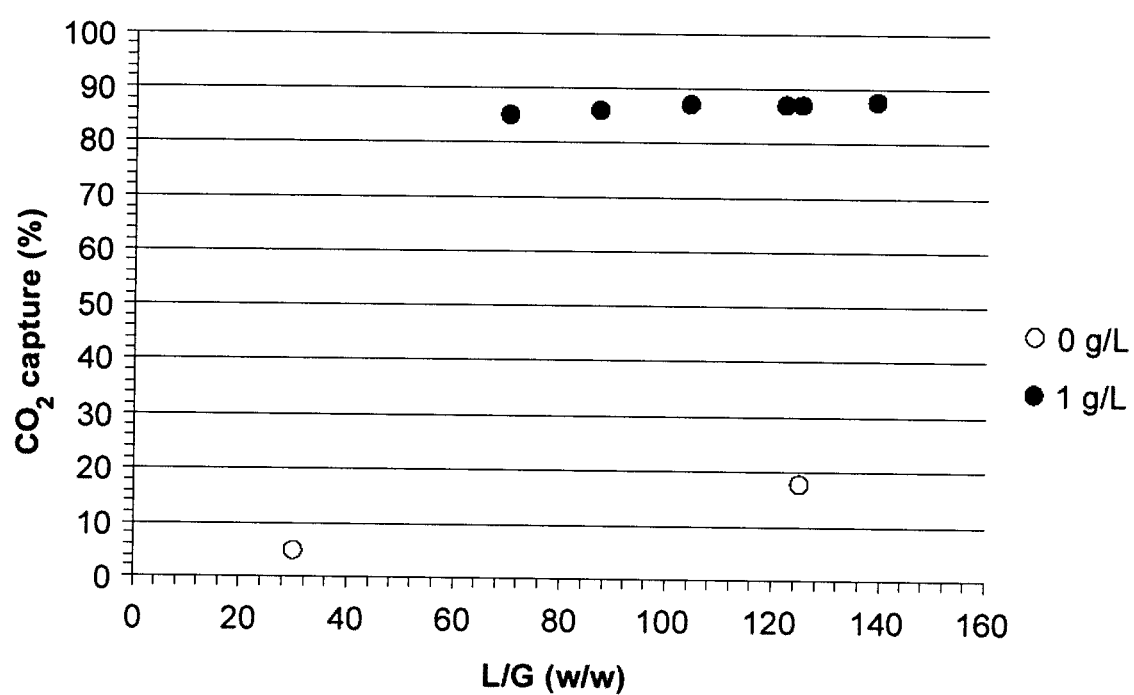
FIG. 13 is a graph showing the percentage of $CO_2$ capture obtained in a rotating packed bed using a 1.45 M $K_2CO_3$ at a $CO_2$ loading of 0.7 mol C/mol K$^+$ at enzyme concentrations of 0 and 1 g/L at different L/G. The rotational speed of the contactor was adjusted at 450 rpm.
Figure 14:
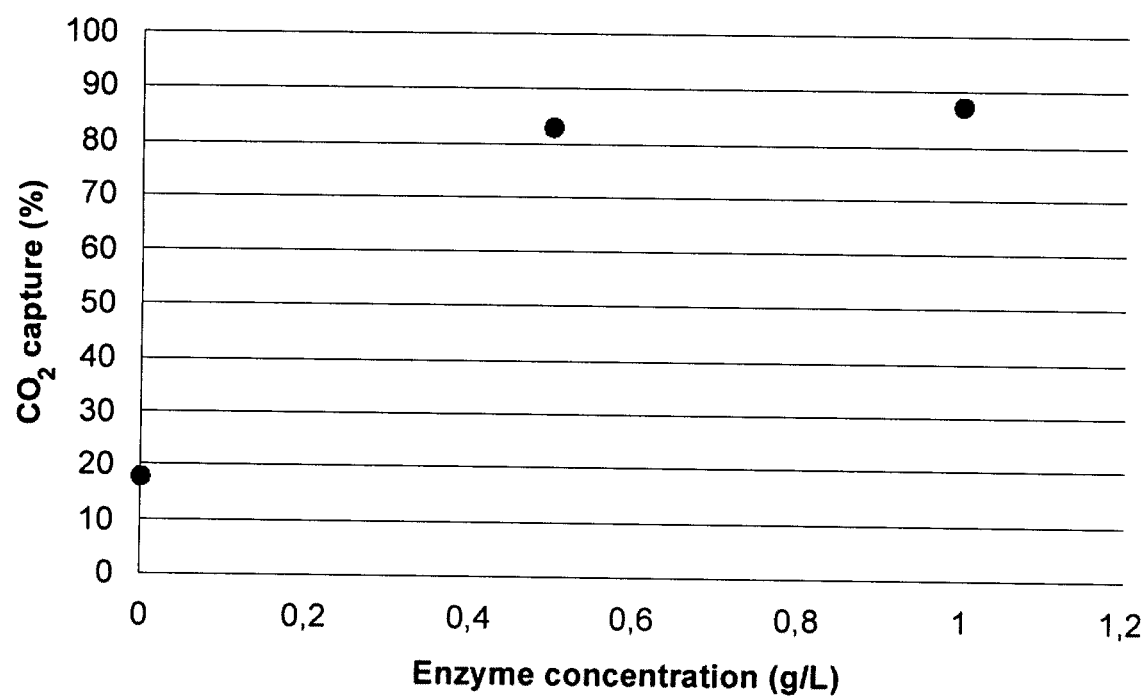
FIG. 14 is a graph showing the percentage of $CO_2$ capture obtained in a rotating packed bed using a 1.45 M $K_2CO_3$ solution at a $CO_2$ loading of 0.7 mol C per mol K$^+$. The RPB is operated at an L/G of 125 g/g and a rotational speed of 450 rpm. Enzyme concentrations are 0, 0.5 and 1 g/L.

In addition to $CO_2$ absorption tests described in Experimentations 3 and 4, further tests were conducted using the same carbonic anhydrase and same rotating packed bed equipment. These tests were aimed at obtaining additional data in intermediate values of L/Gs and at lower values of enzyme concentration, liquid and gas flowrates. Another objective was to validate the impact of rotational speed of the bed. The absorption solution consisted 1.45M potassium carbonate solution ($K_2CO_3$); the $CO_2$ loading of the solution was adjusted to 0.70 mol carbon/mol potassium ions. An antifoam agent, Suppressor 3592 (Hydrite Chemical) a polyol-based dispersion, was added to the carbonate solution at a concentration of 200 mg/L. The $CO_2$ concentration in the gas phase was 9.5% (v/v) dry basis. The L/G ratios were 50, 70, 85, 100, 125, 140 (w/w). The gas flowrate was 60 liters per minute. Tests were conducted at room temperature for 3 enzyme concentrations: 0, 0.5 and 1 g/L. The packed bed rotational speed was adjusted at 450, 600, 750 and 900, 1050 and 1200 rpm. The results are reported as a percentage of $CO_2$ capture in the gas phase. Results are shown in FIGS. 13 and 14. Results on FIG. 13 indicate that for L/G lower or equal to 125, at an enzyme concentration of 1 g/L, the percent of $CO_2$ capture slightly depends on the L/G of the system. And the maximum $CO_2$ capture rate is the maximum achievable value as the liquid phase at the outlet is in equilibrium with the gas phase. Results on FIG. 14 show the impact of increasing the enzyme concentration on the performance of the RPB for an L/G of 125. Results indicate in this case that the maximum performance is reached at 1 g/L enzyme, which corresponds to the high enzyme concentration value or elevated concentration as defined above, under the tests conditions.

The invention claimed is:

1. A biocatalytic process for treating a $CO_2$ containing gas, comprising:
supplying $CO_2$ containing gas into a rotating packed bed (RPB) comprising a reaction chamber;
supplying an absorption solution into the RPB;
contacting the $CO_2$ containing gas and the absorption solution within the reaction chamber, in the presence of carbonic anhydrase, under fluid acceleration conditions of at least 50 m/s$^2$ to convert dissolved $CO_2$ into bicarbonate and hydrogen ions and to form a $CO_2$ depleted gas and an ion enriched solution free of bicarbonate precipitates, wherein the carbonic anhydrase is free in the absorption solution in that the carbonic anhydrase is not immobilized on or in particles flowing with the absorption solution and the carbonic anhydrase flows with the absorption solution; and withdrawing the $CO_2$ depleted gas and an ion enriched solution from the RPB.

2. The biocatalytic process of claim 1, comprising supplying the ion enriched solution to a regeneration unit to produce a regenerated liquid stream and a $CO_2$ gas stream.

3. The biocatalytic process of claim 2, wherein all of the ion enriched solution is supplied directly to the regeneration unit.

4. The biocatalytic process of claim 3, wherein the ion enriched solution passes through a heat exchanger prior to being introduced into the regeneration unit.

5. The biocatalytic process of claim 1, wherein the absorption solution further comprises a defoamer comprising a silicon based compound and the defoamer is provided in a concentration of at least 50 mg/L.

6. The biocatalytic process of claim 5, wherein the carbonic anhydrase is present in an enzyme concentration between about 0.1 g/L and about 2 g/L.

7. The biocatalytic process of claim 5, wherein the carbonic anhydrase is present in an enzyme concentration between about 0.2 g/L and about 1.5 g/L.

8. The biocatalytic process of claim 5, wherein the carbonic anhydrase is present in an enzyme concentration between about 0.5 g/L and about 1 g/L.

9. The biocatalytic process of claim 1, wherein the absorption solution comprises a carbonate compound.

10. The biocatalytic process of claim 9, wherein the carbonate compound comprises a monovalent metal ion.

11. The biocatalytic process of claim 10, wherein the carbonate compound comprises sodium carbonate.

12. The biocatalytic process of claim 10, wherein the carbonate compound comprises potassium carbonate.

13. The biocatalytic process claim 1, wherein the contacting of the $CO_2$ containing gas and the absorption solution is performed in one pass through the reaction chamber.

14. The biocatalytic process of claim 1, wherein packing material in the reaction chamber comprises metal foam.

15. The biocatalytic process of claim 1, wherein packing material in the reaction chamber has between 80% and 95% porosity.

16. The biocatalytic process of claim 1, wherein the rotating packed bed is operated to provide fluid acceleration of at least 335 m/s$^2$.

17. The biocatalytic process of claim 1, wherein the rotating packed bed has a radius of 0.1 m to 0.2 m and is operated with a rotational speed between 450 and 1200 rotations per minute.

18. The biocatalytic process of claim 1, wherein the absorption solution further comprises a defoamer.

19. The biocatalytic process of claim 1, wherein the RPB is operated at a liquid to gas (L/G) ratio that is between about 30 and about 300 on a w/w basis.

20. The biocatalytic process of claim 1, further comprising providing heat to the RPB from low-grade heat via a heat transfer fluid.

21. A biocatalytic process for treating a $CO_2$ containing gas, comprising:

supplying $CO_2$ containing gas into a rotating packed bed (RPB) comprising a reaction chamber;

supplying an absorption solution into the RPB;

contacting the $CO_2$ containing gas and the absorption solution within the reaction chamber, in the presence of carbonic anhydrase, under fluid acceleration conditions of at least 50 m/s$^2$ to convert dissolved $CO_2$ into bicarbonate and hydrogen ions and to form a $CO_2$ depleted gas and an ion enriched solution free of bicarbonate precipitates, wherein the carbonic anhydrase is free in the absorption solution in that the carbonic anhydrase is not immobilized on or in particles flowing with the absorption solution and the carbonic anhydrase flows with the absorption solution; and withdrawing the $CO_2$ depleted gas and an ion enriched solution from the RPB, wherein the absorption solution comprises a defoamer.

22. The biocatalytic process of claim 21, wherein the defoamer is present in the absorption solution at a concentration of 50 to 300 mg/L.

* * * * *

UNITED STATES PATENT AND TRADEMARK OFFICE
CERTIFICATE OF CORRECTION

| | |
|---|---|
| PATENT NO. | : 11,420,159 B2 |
| APPLICATION NO. | : 15/562804 |
| DATED | : August 23, 2022 |
| INVENTOR(S) | : Verma et al. |

It is certified that error appears in the above-identified patent and that said Letters Patent is hereby corrected as shown below:

In the Specification

Column 9, Line 54: Please correct "1000" to read --100° C.,--

Column 15, Line 30: Please correct "1000" to read --100° C.,--

Signed and Sealed this
Thirty-first Day of January, 2023

Katherine Kelly Vidal
*Director of the United States Patent and Trademark Office*